US005637503A

United States Patent [19]
Brigelius-Flohe' et al.

[11] Patent Number: 5,637,503
[45] Date of Patent: Jun. 10, 1997

[54] PLASMIDS, THEIR CONSTRUCTION AND THEIR USE IN THE MANUFACTURE OF A PLASMINOGEN ACTIVATOR

[75] Inventors: Regina E. Brigelius-Flohe' ; Leopold Flohe' , both of Roetgen; Wolfgang Hillen, Erlangen; Gerd J. Steffens, Aachen; Wolfgang Strassburger, Wuerselen; Martin R. F. Wilhelm, Duesseldorf, all of Germany

[73] Assignee: Gruenenthal GmbH, Aachen, Germany

[21] Appl. No.: 551,907

[22] Filed: Jul. 12, 1990

[30] Foreign Application Priority Data

Jul. 19, 1989 [DE] Germany ................... 39 23 866.0

[51] Int. Cl.$^6$ ............................ C12N 15/00; C12P 21/06; C07H 21/02
[52] U.S. Cl. ................... 435/320.1; 435/69.1; 435/215; 435/252.33; 435/69.6; 435/71.1; 536/23.1
[58] Field of Search .................... 435/69.1, 320.1, 435/215, 252.33, 69.6, 71.1; 536/27, 23.1

[56] References Cited

U.S. PATENT DOCUMENTS

| | | | |
|---|---|---|---|
| 4,370,417 | 1/1983 | Hung et al. | 435/212 |
| 4,558,010 | 12/1985 | Hung et al. | 435/212 |
| 4,710,464 | 12/1987 | Belagaje et al. | 435/69.1 |

FOREIGN PATENT DOCUMENTS

| | | | |
|---|---|---|---|
| 92182 | 10/1983 | European Pat. Off. | C12N 15/00 |
| 210279 | 2/1987 | European Pat. Off. | C12N 9/72 |
| 236209 | 9/1987 | European Pat. Off. | C12N 15/00 |
| 277313 | 8/1988 | European Pat. Off. | C12N 15/00 |
| 303028 | 2/1989 | European Pat. Off. | C12N 15/00 |
| WO89/03886 | 5/1989 | WIPO | C12P 21/00 |

OTHER PUBLICATIONS

Brosius (1984), Gene 27, 161–172.
Brosius et al. (1984). PNAS, USA 81, 6929–6933.
Finnegan et al (1982) Mol. Gen. Genet. 185, 344–351.
Krueger et al., Bio Pharm, pp. 40–45 (Mar. 1989).
German Coll. of Microorganisms and Cell Cultures, Catalogue of Strains, Fourth Edition, 1989, pp. 155–156.
Stormo et al., in Maximizing Gene Expression, Butterworth Publ., ed. by Reznikoff et al., Stoneham, MA, (1986) pp. 203, 204, 211.
Ernst, Trends in Biotechnology, 6: 196–199 (1988).
Vieira et al., Gene 19 :259–268 (1982).
Shepard et al., DNA 1: 125–131 (1982).
D. M. Glover, "A Practical Approach", *DNA Cloning*, vol. 1, Chapter 6, pp. 109–135.
J. Meyer et al., "Randomised Double–Blind Trial of Recombinant Pro–Urokinase . . . ", *The Lancet*, pp. 863–868 (Apr. 22, 1989).
Yasuo Hibino et al., "Enhanced Expression of Human Pro–urokinase cDNA in *Escherichia coli*", *Agric. Biol. Chem.*, 52(2), pp. 329–336 (1988).
Holmes et al., "Cloning and Expression of the Gene . . . ", *Bio/Technology*, vol. 138, No. 3, pp. 705–714 (Jun. 1979).

Jorgensen and Reznikoff, "Organization of Structural and Regulatory Genes . . . ", *Journal of Bacteriology*, vol. 138, No. 3, pp. 705–714 (Jun. 1979).
Schollemier et al., "A bidirectionally active signal for termination . . . ", *Nucleic Acids Research*, pp. 4227–4237 (1985).
Adams et al., "Hindered Dialkylamino Nucleoside Phosphite Reagents . . . ", *J. Am. Chem. Soc.*, 105, pp. 661–663 (1983).
Wilhelm and Hollenberg, "Nucleotide sequence of the Bacillus and *Escherichia coli* enzyme", *Nucleic Acids Research*, vol. 13, No. 15, pp. 5717–5722 (1985).
Winkler and Blaber, "Purification Characterization of Recombinant . . . ", *American Chemical Society—Biochemistry*, 25, pp. 4041–4045 ( 1986).
*Nachr. Chem. Tech. Lab.*, 35, pp. 939–940 (1987).
Winnacker, "Gene und Klone", VCH Verlagsgesellschaft, Weinheim, 1985, p. 298.
Christie et al., "Synthetic sites for transcription termination . . . ", *Proc. Natl. Acad. Sci. USA*, vol. 78, No. 7, pp. 4180–4184 (Jul. 1981).
DeBoer et al., "The tac promoter: A functional hybrid derived from the trp and lac promoters", *Proc. Natl. Acad. Sci. USA*, vol. 80, pp. 21–25 (Jan. 1983).
Chemical Abstracts 106:63532c.
Chemical Abstracts 106:208738m.
Chemical Abstracts 107:150137s.
Chemical Abstracts 108:146120j.
Chemical Abstracts 109:2916w.
Chemical Abstracts 110:107601p.
Sato et al., "New Approaches for the High–Level Expression of Human Interleukin–2 cDNA in *Escherichia coli*", *J. Biochem.* 101:525–34 (1987).
Windass et al., "The construction of a synthetic *Escherichia coli* trp promoter and its use in the expression of a synthetic interferon gene", *Nucleic Acids Research* 10:6639–57 (1982).

*Primary Examiner*—Mindy Fleisher
*Attorney, Agent, or Firm*—Evenson, McKeown, Edwards & Lenahan P.L.L.C.

[57] ABSTRACT

Plasmids containing synthetic DNA sequences are described which are suitable for the expression of the intermediate protein of the recombinant scu-PA (i.e., the unglycosylated protein moiety of the single chain prourokinase) in Enterobacteriaceae, especially in *E. coli*, with expression rates far higher than those obtainable according to prior methods. The plasmids comprise operons that include a regulatable, optionally synthetic, promotor, a Shine-Dalgarno sequence, a start codon, a synthetic structural gene with selected codon usage, and downstream of the structural gene, 1 to 2 transcription terminators. The preparation of the plasmids and of synthetic DNA-sequences starting from commercially available plasmids and intermediates is described. The intermediate protein, expressed in high yields by using the plasmids for transforming suitable hosts, may be refolded to produce the therapeutically useful plasminogen activator recombinant scu-PA. This protein also may serve as a starting material for obtaining the recombinant two chain unglycosylated urokinase protein (rtcu-PA) on a large scale by splitting the single chain product.

20 Claims, 27 Drawing Sheets

Figure 1b
pBF 157
Eco RV x Nru I(787bp)
Isolation of the 3348 bp-
fragment
Ligation
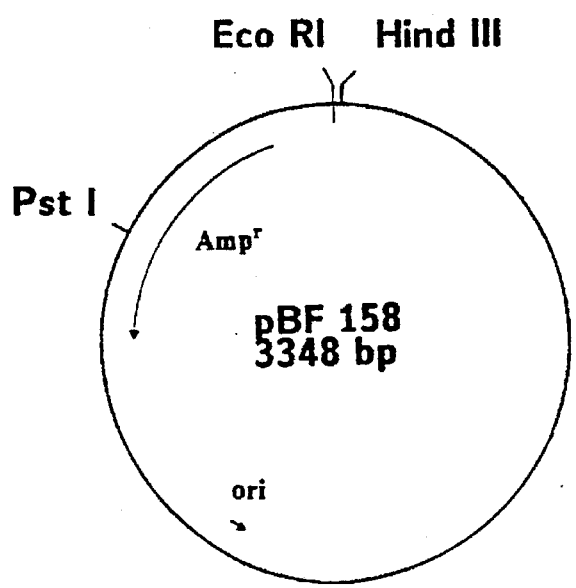
pBF 158
3348 bp

Figure 2

Synthetic multi cloning site

EcoRI

```
  <--------------------------------B1-------------------------
  AATTCATTCTGGTCTGCGATGCTAGTCTAGATAAGGAGGAAATCATATGAGCAATGAACT
      GTAAGACCAGACGCTACGATCAGATCTATTCCTCCTTTAGTATACTCGTTACTTGA
      <--------------------------B1A------------------------

-------------><-------------------------------B2--------------
  TCATCTGCAGCAAGTTCCATCGAACGAGCTCAAATTCCAGTGCGGTCAGCGGCCGTTCTC
  AGTAGACGTCGTTCAAGGTAGCTTGCTCGAGTTTAAGGTCACGCCAGTCGCCGGCAAGAG
  ------------------><------------------B2A-------------

-------------------><---------------------------------------
  GTCTCAACTCTGGTACCTCTTGCGATTTCACAGGTACTAGTTTGCTCTCGCCAGCGTGGA
  CAGAGTTGAGACCATGGAGAACGCTAAAGTGTCCATGATCAAACGAGAGCGGTCGCACCT
  -----------------------------><-----------------------------

B3---------------------------------------->
  TCCGTTCTCACACCAAAGAAATCGATGACCTTCAAGTTCTGCA         HindIII
  AGGCAAGAGTGTGGTTTCTTTAGCTACTGGAAGTTCAAGACGTTCGA
  B3A---------------------------------------->
```

Figure 5

Sequence of the oligonucleotides O1- O19; O1A - O19A

Figure 5a   M2 (O1-O4; O1A-O4A):

NdeI

```
<--------------------------O1-----------------------------><--
  TATGAGCAATGAACTTCATCAAGTTCCATCGAACTGTGACTGTCTAAATGGCGGAACCTG
     ACTCGTTACTTGAAGTAGTTCAAGGTAGCTTGACACTGACAGATTTACCGCCTTGGAC
     <----------------------O1A----------------------------><------

-----------------------O2-----------------------------><--
  CGTTTCTAACAAATATTTCTCTAACATCCACTGGTGTAACTGCCCGAAAAAATTCGGTGG
  GCAAAGATTGTTTATAAAGAGATTGTAGGTGACCACATTGACGGGCTTTTTTAAGCCACC
  -----------------------------O2A----------------------------

--------------------------O3----------------------------
  TCAGCACTGCGAAATCGACAAATCTAAAACCTGCTACGAAGGTAACGGTCACTTCTACCG
  AGTCGTGACGCTTTAGCTGTTTAGATTTTGGACGATGCTTCCATTGCCAGTGAAGATGGC
  -----------><----------------O3A------------------------><------

---------><-----------------------O4---------------------
  TGGTAAGGCTTCTACCGACACCATGGGTCGTCCGTGCCTGCCGTGGAACTCTGCTACCGT
  ACCATTCCGAAGATGGCTGTGGTACCCAGCAGGCACGGACGGCACCTTGAGACGATGGCA
  ------------------------O4A----------------------------

----->
  TCTGCA
  AG         Pst I
  ->
```

```
                <----------------------O5---------------
        GCAGACCTACCACGCTCACCGTTCTGATGCATTGCAGCTGGGTCTGG
Pstl    ACGTCGTCTGGATGGTGCGAGTGGCAAGACTACGTAACGTCGACCCAGACC
        <----------------------O5A--------------------><

-------------><----------------------------O6-------------
GTAAACACAACTACTGCCGTAACCCGGACAACCGTCGTCGTCCGTGGTGCTACGTTCAGG
CATTTGTGTTGATGACGGCATTGGGCCTGTTGGCAGCAGCAGGCACCACGATGCAAGTCC
---------------------O6A-----------------------><----

-------------><--------------------------O7---------
TTGGTCTGAAACCGCTAGTTCAGGAATGCATGGTTCACGACTGCGCTGACGGTAAAAAC
AACCAGACTTTGGCGATCAAGTCCTTACGTACCAAGTGCTGACGCGACTGCCATTTTTG
------------------------------O7A--------------------

-------------------->
CGTCTTCTCCGCCGGAAGAGCT
GCAGAAGAGGCGGCCTTC          SacI
-------------------->
```

```
                                       <------------------------------O8--
           SacI          CAAATTCCAGTGCGGTCAAAAAACCCTACGTCCGCGTT
                         TCGAGTTTAAGGTCACGCCAGTTTTTTGGGATGCAGGCGCAA
                         <------------------------O8A----------------

------------------------------><----------------------
TTAAAATCATCGGTGGTGAGTTCACCACCATCGAAAACCAGCCGTGGTTCGCTGCTATCT
AATTTTAGTAGCCACCACTCAAGTGGTGGTAGCTTTTGGTCGGCACCAAGCGACGATAGA
--------><------------------------O8B------------------

--------------O9--------------------------------------><------
ACCGTCGTCACCGTGGTGGTTCTGTTACCTACGTTTGCGGTGGTTCTCTGATCTCTCCGT
TGGCAGCAGTGGCACCACCAAGACAATGGATGCAAACGCCACCAAGAGACTAGAGAGGCA
------------------------><------------------------O9A------------------

------------------O10-------------------------------
GCTGGGTTATCTCTGCTACCCACTGCTTCATCGACTACCCGAAAAAAGAAGACTACATCG
CGACCCAATAGAGACGATGGGTGACGAAGTAGCTGATGGGCTTTTTTCTTCTGATGTAGC
--------><------------------------O10A------------------

-------->
TTTACCTC           EagI
AAATGGAGCCGG
------------>
```

```
         <---------------------O11--------------------
         GGCCGTTCTCGTTTAAACTCTAACACCCAGGGTGAAATGAAATTCGAAGTTG
Eagl         CAAGAGCAAATTTGAGATTGTGGGTCCCACTTTACTTTAAGCTTCAAC
             <----------------------------O11A-----------

--------><------------------------------------O12----------
AAAACCTGATCCTGCACAAAGACTACTCTGCTGACACCCTGGCTCACCACAACGACATCG
TTTTGGACTAGGACGTGTTTCTGATGAGACGACTGTGGGACCGAGTGGTGTTGCTGTAGC
-------------------------><-------------------------------

---------------------------><-----------------------------
CTCTGCTAAAAATCCGTTCTAAAGAAGGTCGTTGCGCTCAGCCGTCTCGTACCATCCAGA
GAGACGATTTTTAGGCAAGATTTCTTCCAGCAACGCGAGTCGGCAGAGCATGGTAGGTCT
---O12A--------------------------------------><------------

----O13--------------------------------->
CCATCTGCCTGCCGTCTATGTACAACGACCCGCAGTTCGGTAC
GGTAGACGGACGGCAGATACATGTTGCTGGGCGTCAAGC              Kpnl
----------O13A-------------------------->
```

```
                                        <----------------
                                  Kpnl  CTCTTGCGAAATCACCG
                                        CATGGAGAACGCTTTAGTGGC
                                        <--------------------

---O14I------------------><-----------O14II-------------><-----
GTTTCGGTAAAGAAAACTCTACCGACTACCTGTACCCGGAACAGCTGAAAATGACCGTTG
CAAAGCCATTTCTTTTGAGATGGCTGATGGACATGGGCCTTGTCGACTTTTACTGGCAAC
------O14A-----------------------------><---------------------

------------------O15-------------------------><--------------
TTAAACTGATCTCTCACCGTGAATGCCAGCAGCCGCACTACTACGGTTCTGAAGTTACCA
AATTTGACTAGAGAGTGGCACTTACGGTCGTCGGCGTGATGATGCCAAGACTTCAATGGT
-O15A------------------><---------------------O16A------------

-O16I---------------><-----------------------O16II-----------
CCAAAATGCTGTGCGCTGCTGACCCGCAGTGGAAAACCGACTCTTGCCAAGGTGACTCTG
GGTTTTACGACACGCGACGACTGGGCGTCACCTTTTGGCTGAGAACGGTTCCACTGAGAC
--------><---------------------------O16B---------------------

--------->
GTGGTCCA
CACCAGGTGATC        Spel
------------>
```

```
                                        <--------------------------------O17---------------
        CTAGTTTGCTCTCTCCAGGGTCGTATGACCCTGACCGGTATTGTTTCTTGGG
Spel    AAACGAGAGAGGTCCCAGCATACTGGGACTGGCCATAACAAAGAACCC
                                        <------------------------O17A-----------------

-----------------------><-------------------O18-----------------
GTCGTGGTTGCGCTCTGAAAGACAAACCGGGTGTTTACACCCGTGTTTCTCACTTCCTGC
CAGCACCAACGCGAGACTTTCTGTTTGGCCCACAAATGTGGGCACAAAGAGTGAAGGACG
--------><---------------------------O18A-----------------

--->
CGTG
GCACCTAG    BamHI
-------->
```

BamHI

```
        <----------------------------------O19----------------
        GATCCGTTCTCACACCAAAGAAGAAAACGGTCTGGCTCTGTAAGCTAGCCCGCCTA
            GCAAGAGTGTGGTTTCTTCTTTTGCCAGACCGAGACATTCGATCGGGCGGAT
            <------------------------------O19A---------------
```

```
-------------------->
ATGAGCGGGCTTTTTTTTAT            ClaI
TACTCGCCCGAAAAAAATAGC
-------------------->
```

Figure 7a
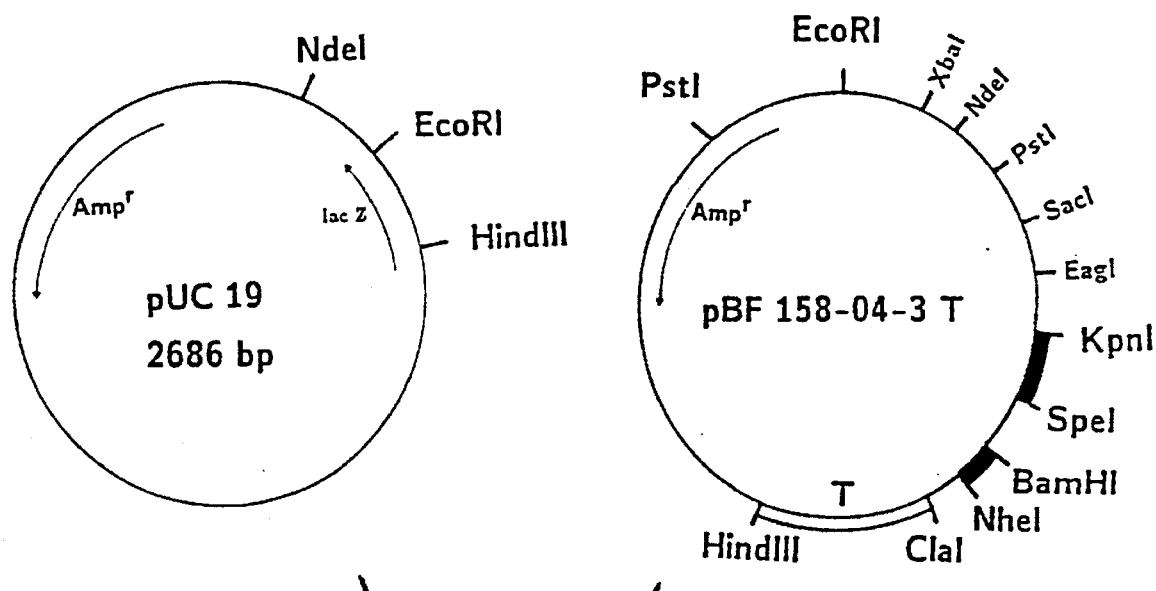
Nde I x Hind III
Isolation of the 2417 bp-fragment
Nde I x Hind III
Isolation of the 712 bp-fragment
Ligation of both fragments
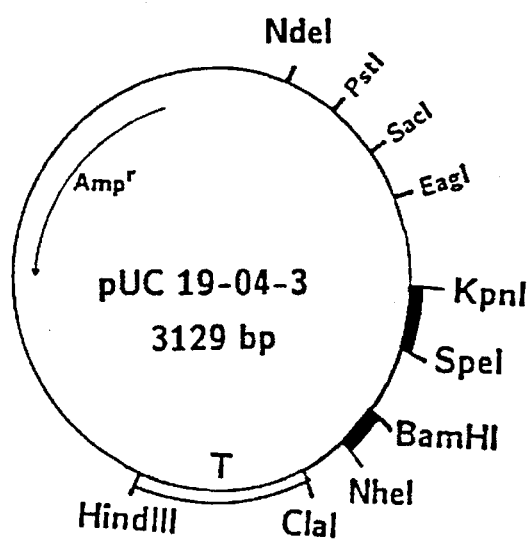

Figure 7b
pUC 19-04-3
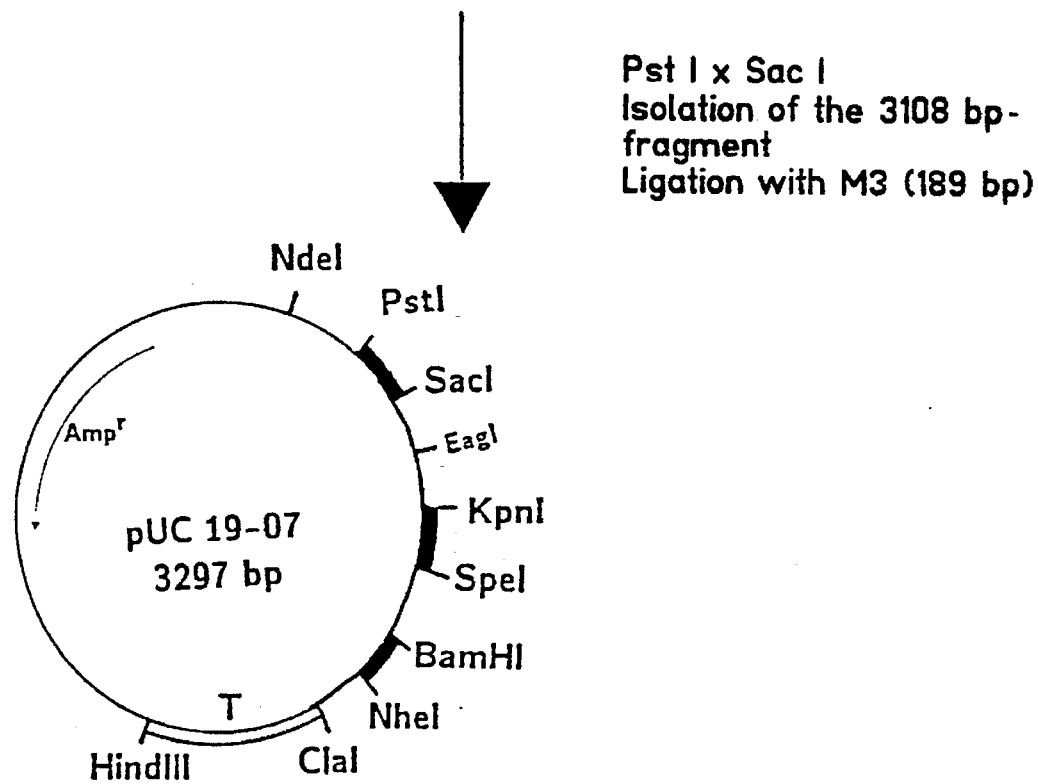
Pst I x Sac I
Isolation of the 3108 bp-fragment
Ligation with M3 (189 bp)
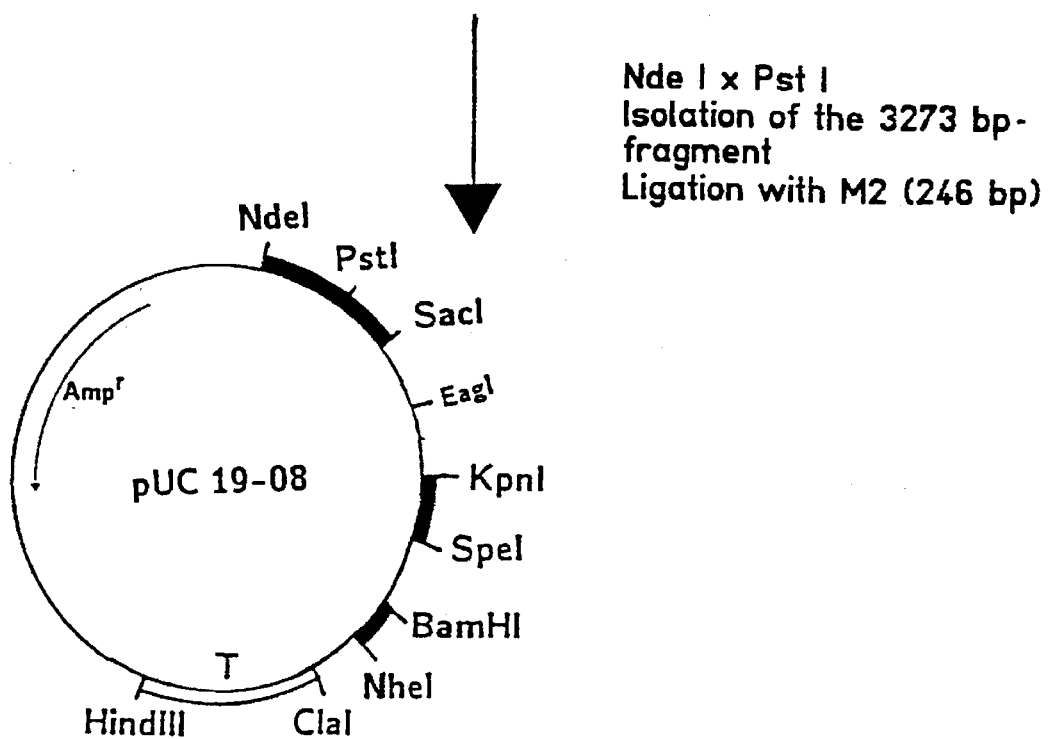
Nde I x Pst I
Isolation of the 3273 bp-fragment
Ligation with M2 (246 bp)

```
                <----------------------------------O21--------------
        AATTCTGAAATGAGCTGTTGACAATTAATCATCGAACTAGTTAACTAGTACGC
EcoRI   GACTTTACTCGACAACTGTTAATTAGTAGCTTGATCAATTGATCATGCG
                <--------------------------------O21A------------
```

```
---------------------->
AAGTTCACGTAAAAAGGGTAT      XbaI
TTCAAGTGCATTTTTCCCATAGATC
-------------------------->
```

DIRECTION OF MIGRATION → rscu-PA intermediate protein

DIRECTION OF MIGRATION →

Figure 13
Fill in - reaction after Nde I - restriction
↓ x NdeI
5' TCTAGATAAGGAGGAAATCA   TATG.. 3'
3' AGATCTATTCCTCCTTTAGTAT   AC.. 5'
fill in - reaction
Ligation
↓
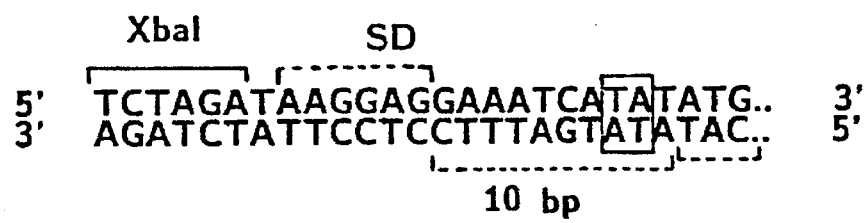

Figure 15a

```
AGTTCACGTAAAAAGGGTATCTAGATAAGGAGGAAATCATATG                                        5
                                                                                  58

Gln Val Pro Ser Asn Cys Leu Asn Gly Ser Asn Glu Leu His                           21
CAA GTT CCA TCG AAC TGT CTA AAT GGC AGC AAT GAA CTT CAT                          106

Asn Lys Tyr Phe Ser Asp Cys Ile His Asn Gly Thr Cys Val Ser                       37
AAC AAA TAT TTC TCT GAC TGT ATC CAC AAT GGA ACC TGT GTT TCT                      154

Gly Gly His Cys Tyr Arg Trp Ser Lys Ala Ser Cys Pro Lys Phe                       53
GGT CAC CAC TGC TAC CGT TGG TCT AAA GCT TCT TGC CCG AAA TTC                      202

Asn Gly His His Phe Tyr Arg Lys Leu Ala Thr Ser Leu Thr Cys Met Gly Tyr Lys Gly    69
AAC GGT CAC CAC TTC TAC CGT AAG GCT ACC TCT CTG ACC TGT ATG GGT TAC AAG           250

Pro Cys Leu Arg Asn Ala Gln Leu Gly Arg Arg Leu Gly Leu Pro Pro Met Gln Val Arg    85
CCG TGC CTG CGT AAC GCA CAG CTG GGT CGT CGT CTG GGT CCG CCG ATG CAG GTT CGT       298

Ala His Arg Ser Asp Asn Ala Ser Pro Met Glu Gly Cys Val Gln Ala Asp Cys Gly       101
GCT CAC CGT TCT GAT AAC GCA TCT CCG ATG GAA GGT TGT GTT CAG GCT GAC TGT GGT       346

Cys Arg Pro Pro Asp Ala Pro Glu Pro Pro Phe Arg Arg Glu Lys Phe His Ala Phe       117
TGC CGT CCG CCG GAC GCA CCG GAA CCG CCG TTC CGT CGT GAA AAA TTC CAC GCA TTC       394

Gly Leu Lys Lys Pro Pro Ser Arg Arg Arg Arg Phe Phe Lys Met Val Leu Lys Ala       133
GGT CTG AAA AAA CCG CCG TCT CGT CGT CGT CGT TTT TTT AAA ATG GTT CTC AAA GCT       442

Gly Lys Lys Thr Leu Leu Arg Gln Glu Glu Ile Ile Ile Lys Ile Leu Lys Gly           149
GGT AAA AAA ACC CTA CTA CGT CAG GAA GAG ATC ATC ATC AAA CTC ATC AAA GGT           490

Gln Asn Glu Asn Leu Thr Thr Val Ile Ala Ala Ala Gly Tyr Arg Glu Phe Thr           165
CAA AAC GAA AAC CTA ACC ACC GTT ATC GCT GCT GCT GGT TAC CGT GAG TTC ACC           538

Gly Gly Ser Val Thr Thr Tyr Gly Gly Ser Tyr Arg Arg Ser Leu Ile His Arg           181
GGT GGT TCT GTT ACC ACC TAC GGT GGT TCT TAC CGT CGT TCT CTG ATC CAC CGT           586

Trp Val Ile Ser Ala Thr Ala His Cys Phe Ile Asp Tyr Pro Lys Pro Lys Glu           197
TGG GTT ATC TCT GCT ACC GCT CAC TGT TTC ATC GAC TAC CCG AAA CCG AAA GAA           634

Phe Cys Pro Phe Leu Asn Lys Arg Thr Ser Leu Gly Phe Gln Lys Ala Tyr Lys Glu       213
TTC TGC CCG TTC CTA AAC AAA CGT ACC TCT CTG GGT TTC CAG AAA GCT TAC AAA GAA       682
```

| Asp | Tyr | Ile | Val | Tyr | Leu | Gly | Arg | Ser | Asn | Thr | Gln | 229 |
| GAC | TAC | ATC | GTT | TAC | CTC | GGC | CGT | TCT | AAC | ACC | CAG | 730 |
| Gly | Glu | Met | Lys | Phe | Glu | Val | Arg | Leu | His | Lys | Asp | Tyr | 245 |
| GGT | GAA | ATG | AAA | TTC | GAA | GTT | GAA | CTG | CAC | AAA | GAC | TAC | 778 |
| Ser | Ala | Asp | Thr | Leu | Ala | His | Asn | Ala | Ile | Leu | Lys | Ile | 261 |
| TCT | GCT | GAC | ACC | CTG | GCT | CAC | AAC | GCT | ATC | CTA | AAA | ATC | 826 |
| Arg | Lys | Glu | Lys | Gly | Arg | Cys | Ala | Gln | Pro | Ser | Thr | Ile | Gln | Thr | 277 |
| CGT | AAA | GAA | AAA | GGT | CGT | TGC | GCT | CAG | CCG | TCT | ACC | ATC | CAG | ACC | 874 |
| Ile | Cys | Leu | Pro | Ser | Met | Arg | Tyr | Asn | Pro | Gln | Thr | Arg | Phe | Gly | Thr | Leu | Ser | Cys | 293 |
| ATC | TGC | CTG | CCG | TCT | ATG | CGT | TAC | AAC | CCG | CAG | ACC | CGT | TTC | GGT | ACC | CTG | TCT | TGC | 922 |
| Glu | Ile | Thr | Gly | Phe | Gly | Met | Asp | Ser | Thr | Thr | Asp | Tyr | Leu | Tyr | Pro | 309 |
| GAA | ATC | ACC | GGT | TTC | GGT | ATG | GAC | TCT | ACC | ACC | GAC | TAC | CTG | TAC | CCG | 970 |
| Gly | Gln | Leu | Lys | Met | Ala | Ser | Leu | Asn | Ile | Ser | Leu | Ile | His | Arg | Glu | Cys | 325 |
| GGT | CAG | CTG | AAA | ATG | GCT | TCT | CTG | AAC | ATC | TCT | CTG | ATC | CAC | CGT | GAA | TGC | 1018 |
| Gln | Gln | Pro | His | Tyr | Gly | Ser | Val | Thr | Thr | Lys | Met | Leu | Cys | 341 |
| CAG | CAG | CCG | CAC | TAC | GGT | TCT | GTT | ACC | ACC | AAA | ATG | CTG | TGC | 1066 |
| Ala | Ala | Pro | Gln | Trp | Lys | Ser | Asp | Thr | Cys | Arg | Met | Thr | Asp | Ser | Gly | 357 |
| GCT | GCT | CCG | CAG | TGG | AAA | TCT | GAC | ACC | TGC | CGT | ATG | ACC | GAC | TCT | GGT | 1114 |
| Gly | Pro | Leu | Val | Cys | Leu | Ala | Leu | Gln | Gly | Arg | Met | Lys | Asp | Thr | Gly | Ile | 373 |
| GGT | CCA | CTA | GTT | TGC | CTC | GCT | CTG | CAG | GGT | CGT | ATG | AAA | GAC | ACC | GGT | ATT | 1162 |
| Val | Ser | Trp | Gly | Arg | Gly | Cys | Ala | Leu | Lys | Asp | Lys | Pro | Gly | Val | Tyr | 389 |
| GTT | TCT | TGG | GGT | CGT | GGT | TGC | GCT | CTG | AAA | GAC | AAA | CCG | GGT | GTT | TAC | 1210 |
| Thr | Arg | Val | Ser | His | Phe | Leu | Pro | Trp | Ile | Arg | Ser | His | Thr | Lys | Glu | 405 |
| ACC | CGT | GTT | TCT | CAC | TTC | CTG | CCG | TGG | ATC | CGT | TCT | CAC | ACC | AAA | GAA | 1258 |
| Glu | Asn | Gly | Leu | Ala | Leu | 411 |
| GAA | AAC | GGT | CTG | GCT | CTG | TAAGCTAGCCCGCCTAATGAGCGGGCTTTTTTTATCGAT | 1316 |

PLASMIDS, THEIR CONSTRUCTION AND THEIR USE IN THE MANUFACTURE OF A PLASMINOGEN ACTIVATOR

FIELD OF THE INVENTION

The present invention relates to construction and use of plasmids in the manufacture of the recombinant single chain urinary plasminogen activator "recombinant scu-PA".

BACKGROUND OF THE INVENTION

Plasminogen activators are of great importance in treating occlusions of blood vessels by fibrin clots, as in acute myocardial infarction, pulmonary embolism, arterial thromboembolism and other clinical conditions.

Since about 1951 it has been known that human urine contains a proteolytic enzyme which by limited proteolytic activates plasminogen to plasmin, i.e., the enzyme which degrades fibrin to soluble polypeptides and thus causes the dissolution of the fibrin component of blood clots. This plasminogen activator first isolated from urine in 1951 was named urokinase. Later several different forms of urokinase were described, which all turned out to be related to the same precursor molecule. This zymogen "prourokinase" has been known since at least 1977. The primary structures of the two major forms of urokinase and the structure of prourokinase were elucidated, however, only in 1982 and 1984, respectively. Prourokinase has a single chain structure. Therefore it was designated scu-PA (single chain urinary plasminogen activator). This scu-PA consists of 411 amino acids, and in its naturally occurring form it is glycosylated at the amino acid in position 302 of the protein chain.

Several papers describe the production of the unglycosylated protein moiety of scu-PA by recombinant techniques, in *Escherichia coli* (hereinafter *E. coli*), which is designated as "recombinant scu-PA" (recombinant scu-PA; proposed INN "Saruplase"). In a randomized double-blind therapeutic trial on 401 patients, recombinant scu-PA proved to be more efficient in thrombolysis and better tolerated than conventional fibrinolytic agents (see, for example, *The Lancet*, Apr. 22, 1989, pp. 863 to 868).

As described in various publications, procaryotic organisms can be used to produce the unglycosylated plasminogen activator recombinant scu-PA. The processes known for the production of the recombinant scu-PA involve the expression of the scu-PA structural gene obtained from human tissues. Unfortunately, in these processes only very low expression rates are obtained. These low yields make impossible economically feasible large scale production of the desired product. For instance, Hibino et al., in Agric. Biol. Chem. 52:329–336 (1988), obtained an expression of only 2% from recombinant *E. coli* when calculated per amount of total bacterial protein. Other publications such as, for example, the European patent application published under number 00 92 182 A2 and Holmes et al., Biotechnol. 3:923–929 (1985) give no precise values of the expression rates obtained. Reproduction of these experiments in different bacterial strains, however, also has yielded recombinant scu-PA expression of less than 2% of the bacterial protein.

As in most cases of expressing eukaryotic proteins in bacteria, the recombinant scu-PA protein chain is produced by the transformed bacterial cell in the form of inclusion bodies consisting of denatured protein designated hereinafter as "intermediate protein". This intermediate protein, after isolation, must be renatured ("refolded") by chemical treatment to form the correct tertiary structure of recombinant scu-PA that is suitable for use as a thrombolytic agent. To determine the amount of recombinant scu-PA formed, the resulting product may be treated with plasmin to transform recombinant scu-PA to recombinant (unglycosylated) two chain urokinase ("rtcu-PA"), the enzymatic activity of which is then determined and may serve as a measure of the amount of recombinant scu-PA formed. Of course, it is also possible to determine the amount of intermediate protein formed or the amount of recombinant scu-PA directly, for example, by densitometric scanning of the total bacterial proteins after electrophoretic separation, and thereby determine the expression rate.

Despite a great deal of work which has been done in the art, there remains a need for means and techniques for expressing scu-PA at rates which facilitate economically feasible production of recombinant scu-PA.

SUMMARY OF THE INVENTION

The objects of the invention are achieved by providing an operon for use in the manufacture of the human recombinant single chain urinary plasminogen activator (recombinant scu-PA) comprising in 5' to 3' order the following operatively linked elements: a regulatable promotor, a Shine-Dalgarno sequence effective as a ribosomal binding site, a translational start codon, a synthetic structural gene for said scu-PA, and downstream of the structural gene at least one transcription terminator, and a plasmid comprising such an operon which is suitable for expressing scu-PA protein in species of Enterobacteriaceae.

According to preferred aspects of the invention, within said structural gene, a triplet selected from the group consisting of ATT and ATC is utilized as the codon for isoleucine; a triplet selected from the group consisting of GTT, GTA and GTG is utilized as the codon for valine; a triplet selected from the group consisting of CCT, CCA and CCG is utilized as the codon for proline; a triplet AAA is utilized as the codon for lysine; a triplet selected from the group consisting of CGT and CGC is utilized as the codon for arginine; and a triplet selected from the group consisting of GGT and GGC is utilized as the codon for glycine. Most especially, the triplet CGT is utilized as the codon for arginine; the triplet CTG is utilized as the codon for leucine; the triplet GTT is utilized as the codon for valine; the triplet CCG is utilized as the codon for proline; and the triplet GGT is utilized as the codon for glycine.

In accordance with further aspects of the invention, the objects are achieved by providing a process for producing a plasmid as described above comprising the step of: (i) removing the nic/bom-region and mutationally inactivating the tetracycline resistance gene of the plasmid pBR 322; (ii) inserting a multi-cloning site having the nucleotide sequence of FIG. 2 between the pBR 322 restriction sites Eco RI and Hind III; and (iii) inserting by means of the multi-cloning site a transcription terminator, a synthetic gene encoding scu-PA, and a Trp-promotor such that the gene is operatively linked to the promoter and the terminator.

In accordance with yet another aspect of the invention there is provided a process for producing a plasmid by enlarging the spacing between the Shine-Dalgarno sequence and the start codon, comprising cleaving a plasmid with the restriction enzyme Nde I, filling in the resulting sticky ends, and ligating the resulting blunt ends.

There is also provided a process for producing plasminogen activator recombinant scu-PA comprising the steps of: transforming cells of an enterobacterial strain with a plasmid as described above, inducing expression of said scu-PA structural gene in said cells or their progeny, separating the resulting intermediate protein of recombinant scu-PA from said cells, solubilizing said intermediate protein, and refolding said intermediate protein by the action of a redox system to form recombinant scu-PA.

BRIEF DESCRIPTION OF THE DRAWINGS

The invention will be explained in further detail with reference to the accompanying drawings in which:

FIGS. 1a and 1b show the construction of the plasmid pBF 158 starting with the commercially available plasmid pBR 322. In this construction the nic/bom region and a large part of the tetracycline resistance gene have been removed.

FIG. 2 presents nucleotide sequence of the synthetic "multi-cloning site".

FIGS. 5a through 5g present the nucleotide sequences of the synthetic fragments for constructing the gene coding for human scu-PA, as described in Examples 1(d) to 1(f) and shown in FIGS. 6, 7 and 9.

FIGS. 7a to 7c summarize the construction of the plasmid pBF 158-08 T by using an auxiliary construction in the plasmid pUC 19 (see, for example, Example 1(e)).

FIG. 8 presents the nucleotide sequence of the synthetic Trp-promotor.

FIG. 13 illustrates an enlargement of the distance between the Shine-Dalgarno sequence (SD) and the start codon ATG from 8 to 10 bases by "fill in" of the Nde I restriction sites followed by ligation of the resulting blunt ends.

FIGS. 15a and 15b present the complete nucleotids sequence of the scu-PA structural gene; the amino acids corresponding to the respective codons are indicated in the three letter code.

DETAILED DESCRIPTION OF THE PREFERRED EMBODIMENTS

Figure 1A:
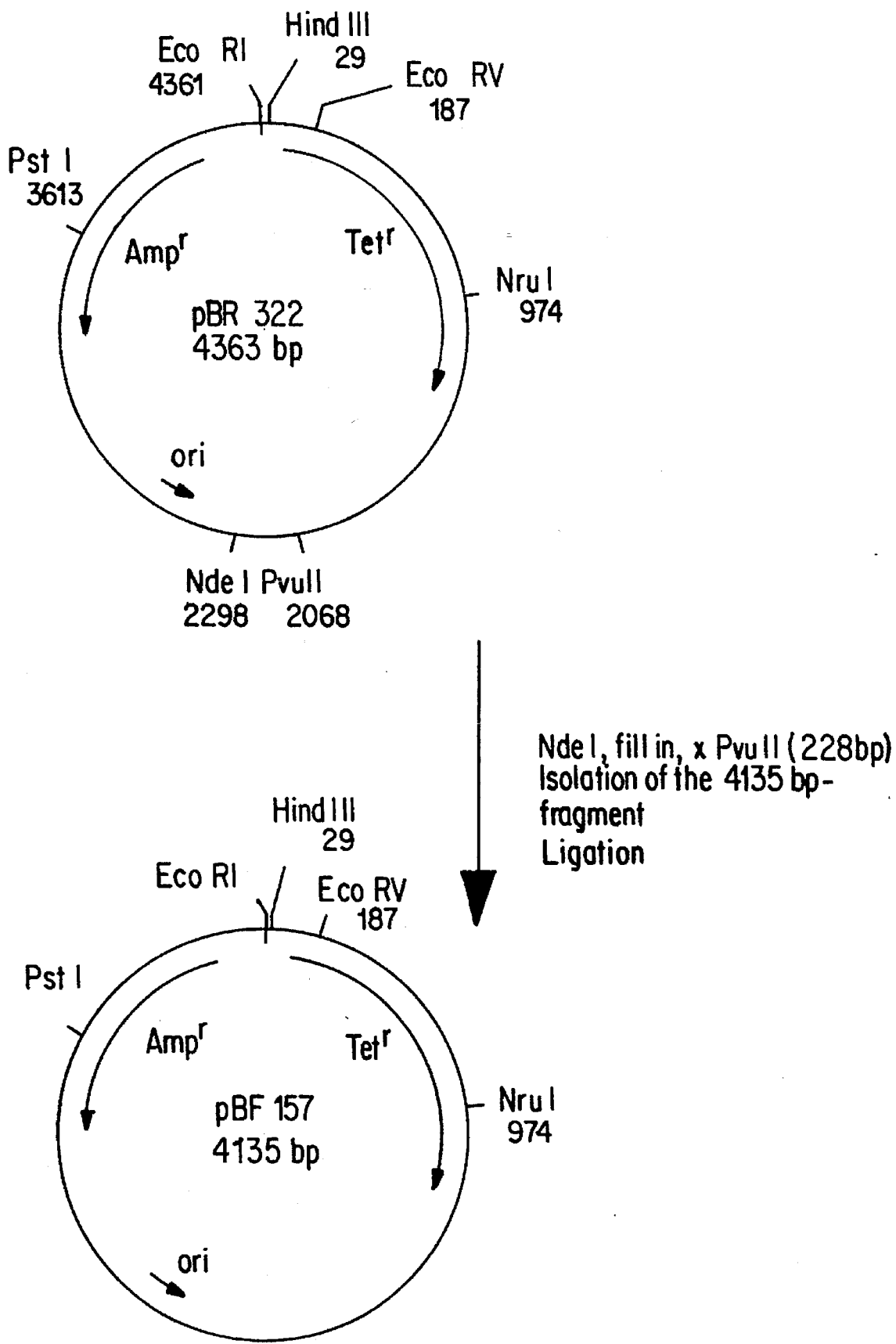

The present invention relates to construction and use of plasmids for the production of the recombinant single chain urinary plasminogen activator known as "recombinant scu-PA". According to the present invention, the undesired formation of stable secondary structures between the structural gene and the controlling region is substantially prevented by the use of selected codons for specific amino acids in the synthetic structural gene and by selection of the proper characteristics of the controlling region in the operon. Surprisingly, it has been found that bacteria transformed with plasmids according to the present invention give expression rates many times higher than those observed after transforming the identical hosts with plasmids known in the art. Therefore, the plasmids of this invention are far more useful for the preparation of the intermediate (insoluble, denatured) protein of the recombinant scu-PA than all plasmids previously known. Now for the first time the present invention readily provides sufficient amounts of the recombinant scu-PA to allow application of previously known methods to split recombinant scu-PA to form rtcu-PA species of high or low molecular weight on an industrial scale (for example, using treatment with plasmin as already mentioned above for analytical applications).

Accordingly, the present invention relates to an operon for use in the manufacture of the human recombinant single chain urinary plasminogen activator comprising in 5' to 3' order the following operatively linked alements: a regulatable (inducible) promotor, a Shine-Dalgarno sequence that is effective as ribosomal binding site, a translational start codon, a synthetic structural gene for the scu-PA and, downstream of the structural gene, at least one transcription terminator. Preferably two successive transcription terminators are present in the operon. Preferred terminators are the trp A terminator and the tet A/orf L terminator from Tn 10 (see, for example, Schollmeier, et al., *Nuc. Acids Res.* 13:4227–4237 (1985)). The regulatable promotor preferably is the Trp-promotor or the Tac-Promotor. In the controlling region of the operon according to the present invention, the distance between the Shine-Dalgarno sequence and the start codon is in the range of from 6 to 12, preferably from 8 to 10, nucleotides. The operon is contained in a DNA fragment that can be inserted into various plasmids which are autonomously replicable in Enterobacteriaceae, preferably in *E. coli*.

In the construction of the structural gene to be incorporated into the plasmids according to the present invention, preferably the triplets listed in the following table and coding for the respective amino acids are utilized.

| Amino acid | triplet |
|---|---|
| arginine | CGT |
| leucine | CTG |
| valine | GTT |
| proline | CCG |
| glycine | GGT |

On the other hand, it is preferred in the construction of the structural gene to avoid as far as possible the use of the codons for the respective amino acids that are listed in the following table.

| Codon to be avoided | amino acid |
|---|---|
| ATA | isoleucine |
| GTC | valine |
| CCC | proline |
| AAG | lysine |
| AGG, AGA, CGG, CGA | arginine |
| GGA, GGG | glycine |

To fall within the scope of the present invention, not all of the above features have to be incorporated in the construction of the operon. For example, the codon preferences defined by the two tables above do not need to be strictly applied in every possible instance. Instead, it is necessary only to incorporate sufficient features (i.e., the above selected codons for specific amino acids in the structural gene and the characteristics of the controlling region in the operon described above) such that the undesired formation of stable secondary structures between the structural gene and the controlling region is significantly reduced. Preferably, sufficient modifications of the operon are made according to the present invention such that formation of the undesirable secondary structures, which reduce the efficiency of expression of the structural gene, are substantially prevented, as illustrated, for instance, by the particular constructs in the following Examples.

To prepare the synthetic structural gene, first, for example, oligonucleotides containing 40 to 80 bases are synthesized in single stranded form. Preferably these are obtained by the solid phase oligonucleotide synthesis method of Adams et al. (Adams, S. P., Kavka, K. S., Wykes, E. I., Holder, S. B., Gallupi, G. R.: *J. Am. Chem. Soc.* 105:661–663 (1983)) on a 1 µmole scale by means of a DNA-synthesizer (model "BioSearch 8600", from New Brunswick Scientific Co.). As the monomer building blocks of choice commercially available β-cyanoethyl-protected diisopropylamino phosphoramidites of the respective deoxyribo-nucleotides are used in the syntheses. After being cleaved from the solid support, the crude and still trityl-bearing strands are desalted and prepurified under sterile conditions by gel filtration and then submitted twice to reverse phase HPLC. The respective main products are detritylated and then purified twice more by reverse phase HPLC to give the desired oligonucleotides in highly pure form as determined by gel electrophoretic analysis (PAGE).

Groups of 4 to 9 of these single stranded oligonucleotides are then used to obtain double-stranded fragments containing about 200 base pairs. This is achieved by phosphorylating (for example, by treatment with T4-polynucleotide kinase) those single stranded oligonucleotides not destined to form the termini of the desired fragments at their 5' termini, by annealing the respective complementary strands with the unphosphorylated oligonucleotides forming the termini, and by ligation. The resulting double stranded clonable fragments are inserted into suitable linearized vectors. The remainder of the procedure is described in detail in the following Examples which are provided for illustration purposes only and are not intended to limit the scope of this invention.

The abbreviations used hereinafter have the following meanings:

| bp | base pairs |
|---|---|
| DE 52 | anion exchanger (Whatman) |
| EDTA | ethylenediaminetetraacetic acid |
| IPTG | isopropyl-β-D-thiogalactopyranoside |
| PAGE | polyacrylamide gel electrophoresis |
| PU | Ploug units |
| SDS | sodium dodecylsulfate |
| S.D.-sequence | Shine-Dalgarno sequence |
| Tris-HCl | tris(hydroxymethyl)aminomethane hydrochloride |
| Tween 80 | polyoxyethylene (20) sorbitan monooleate |

As starting material for the construction of the plasmids according to the invention preferably the commercially available plasmid pBR 322 (4363 bp) is used. In a preferred embodiment of the invention the nic/bom region and/or the tetracycline resistance gene are eliminated from this plasmid. It is not necessary to remove the tetracycline resistance gene completely. Instead, it is sufficient to eliminate or otherwise mutate only so much of this gene that the plasmid no longer is able to transfer tetracycline resistance to bacteria transformed therewith. One skilled in the art will appreciate that the plasmid will no longer be able to transfer tetracycline resistance whenever the tetracycline resistance gene has been mutated not only by deletion, but in any manner such that the plasmid does not express tetracycline resistance (i.e., by mutational inactivation). By these measures (removal of the nic/bom region and mutational inactivation of the tetracycline resistance gene) a so-called "high security plasmid" is obtained.

In the preferred strategy for the construction of a plasmid according to this invention, the next step comprises the insertion of a synthetic "multi-cloning site" between the restriction sites Eco RI and Hind III of the modified plasmid pBR 322 (with the deletions as explained above) or of another of the known appropriate plasmids named hereinafter. This multi-cloning site (see, for example, FIG. 2) comprises a predetermined order of successive restriction sites. The bases bridging the restriction sites are chosen arbitrarily with the exception of the sequence between Xba I and Nde I which contains the ribosome binding site (Shine-Dalgarno sequence) from the *Bacillus subtilis* Xyl operon, 5'-AAGGAG-3' (Wilhelm, et al. *Nuc. Acids Res.* 13: 5717–5722 (1985)) as well as, spaced at predetermined distance from the S.D.-sequence, the translation start codon ATG. The bases GAAAT following the S.D.-sequence are used according to Wilhelm et al., supra. and connected to the sequence CATATG, a Nde I restriction site.

Thus the distance between the S.D.-sequence and the start codon ATG amounts to 8 base pairs. For technical reasons the distances between the several restriction sites should amount to at least about 20 nucleotides as this size facilitates removal of undesired fragments formed in the following steps.

By means of this multi-cloning site restriction sites are inserted into the plasmid which—after optionally inserting a transcription terminator—enable the successive insertion of partial sequences of the scu-PA structural gene, preferably starting from the C-terminus of the desired protein, i.e. from the 3'-terminus of the DNA strand to be prepared, as well as the insertion of a Trp-promotor. This Trp-promotor may be obtained by synthesis, by isolation from another plasmid or it may be commercially available.

The complete nucleotide sequence of the scu-PA structural gene prepared in this way is shown in FIG. 15 in which the amino acids corresponding to the respective codons are also indicated in three letter code.

From a plasmid constructed as described above other plasmids according to the present invention may be prepared by cleaving this plasmid with the restriction endonucleases Eco RI and Hind III to isolate a fragment comprising the synthetic scu-PA structural gene together with all regulatory elements. Thereafter, this fragment is inserted into another plasmid which is autonomously replicable in Enterobacteriaceae, preferably in E. coli, and which had been linearized and shortened by cleavage with Eco RI and Hind III. By following in principle the same approach, but using the restriction sites for Eco RI and Xba I, it is possible to exchange promoters, for example, the Trp-promotor for the Tac-promotor (and vice versa) in a plasmid according to the present invention.

Other known and commercially available plasmids suitable as starting materials in the present invention include those containing singular Eco RI and Hind III restriction sites such as, for example, pUC 9, pUC 12, pUC 13, pUC 18, pUC 19 and others that are known in the art.

Plasmids according to the present invention in which the distance between the Shine-Dalgarno sequence and the start codon ATG is enlarged may be obtained from a plasmid constructed as described above (in which this distance, for example, is 8 nucleotides) by cleavage with Nde I, "fill in" of the resulting cleavage sites and, finally, ligation of the resulting blunt ends, so that the desired plasmid is obtained in which the distance between the S.D.-sequence and the start codon is enlarged, for example, to 10 nucleotides.

As mentioned above, transforming bacteria with plasmids according to the invention results in expression rates several times higher than those achievable by transformation with plasmids known and used in the prior art.

The transformation of suitable competent host organisms with plasmids according to the invention is performed according to standard methods known in the art. Suitable host cells for the expression of a plasmid according to the invention include strains of the species E. coli or of a related Enterobacterium such as a strain of one of the species Pseudomonas, Salmonella, Enterobacter, Klebsiella or Serratia.

Preferred host organisms are strains of the species E. coli such as E. coli GRT-I and especially those of the subgroup K12 such as E. coli K12 JM101 (ATCC 33876), E. coli K12 JM103 (ATCC 39403), E. coli K12 JM105 (DSM 4162), E. coli K12 ATCC 31446, E. coli K12 DM 1 (ATCC 33849) and others.

Expression in E. coli-expression systems containing the Tac-promotor may be induced for example, by adding lactose or by withdrawal of glucose or preferably by adding isopropyl-β-D-thiogalactopyranoside.

If, however, the plasmid contains the Trp-promotor the induction preferably is effected by adding indoleacrylic acid, indoleacetic acid or indolepropionic acid. Of course, other inducers known in the art may also be used.

When the desired density of the cell mass has been reached and the expression has been induced, the cells are harvested by centrifugation. The cell mass is suspended in an aqueous salt solution and homogenized, for example, by means of a homogenizer in which the cells are destroyed by pressure differences. The mixture is centrifuged again to separate insoluble contents, so that a residue consisting of the intermediate protein of recombinant scu-PA and of insoluble cell fragments is obtained. When this residue is treated with guanidine hydrochloride solution the intermediate protein is solubilized. The protein is then treated with a redox system (for instance a system then containing reduced and oxidized glutathione) causing the formation of the correct natural conformation, i.e. the correct tertiary structure of the desired recombinant scu-PA. The resulting mixture contains the recombinant scu-PA in dissolved form. The recombinant scu-PA may be isolated from this solution in pure form in a usual manner as, for instance, by chromatography followed by lyophilization.

For analytical purposes it is convenient to transform strains of E. coli with the plasmid whose properties are to be tested, to cultivate these strains until a predetermined optical density of the cell suspension has been reached, and then to induce the expression of the intermediate protein of recombinant scu-PA by adding a suitable inducer. After an appropriate cultivation time aliquots of the fermentation mixture are taken, and the cells obtained by centrifugation are destroyed by treatment with lysozyme (1 mg of lysozyme per ml of 50 Mm Tris-HCl buffer of pH 8.0, 50 mM EDTA and 15% saccharose). The homogenate of the lysed cells is solubilized by treatment with 4 to 5M guanidine hydrochloride solution. After dilution to 1.2M guanidine hydrochloride, the solution is subjected for 2 to 5 hours to the refolding reaction by addition of a reducing agent such as glutathione, mercaptoethanol or cysteine (also see, for example, Winkler et al., *Biochem.* 25:4041–4045 (1986)). The resulting single chain recombinant scu-PA is transformed to two-chain rtcu-PA by addition of plasmin. The activity of this rtcu-PA then is assayed using the substrate S2444 (pyro Glu-Gly-Arg-p-nitroanilide; Kabi Diagnostika, Sweden) which is split by active two chain urokinases. The recombinant scu-PA is activated to rtcu-PA in 50 mM Tris buffer, 12 mM sodium chloride, 0.02% Tween 80 at pH 7.4 and 37° C.

The ratio of the recombinant scu-PA to plasmin should be from about 100:1 to 1,500:1 (calculated on molarity) or from about 8,000:1 to 36,000:1 (calculated on enzyme units). The assay is performed at 37° C. in 50 mM Tris buffer having a pH of 8.8 containing 38 mM sodium chloride, 0.36 μM aprotinine (to inhibit the plasmin activity) and 0.27 mM S2444 at 37° C. Depending upon the recombinant scu-PA content of the test sample, the reaction is stopped by addition of 50% acetic acid after an incubation period of 5 to 60 minutes, after which the extinction at 405 nm is determined. According to the specifications given by the manufacturer of the substrate S2444, under these conditions a change in extinction of 0.05 per minute at 405 nm represents an activity of 25 Ploug units/ml of the test solution.

Figure 10:
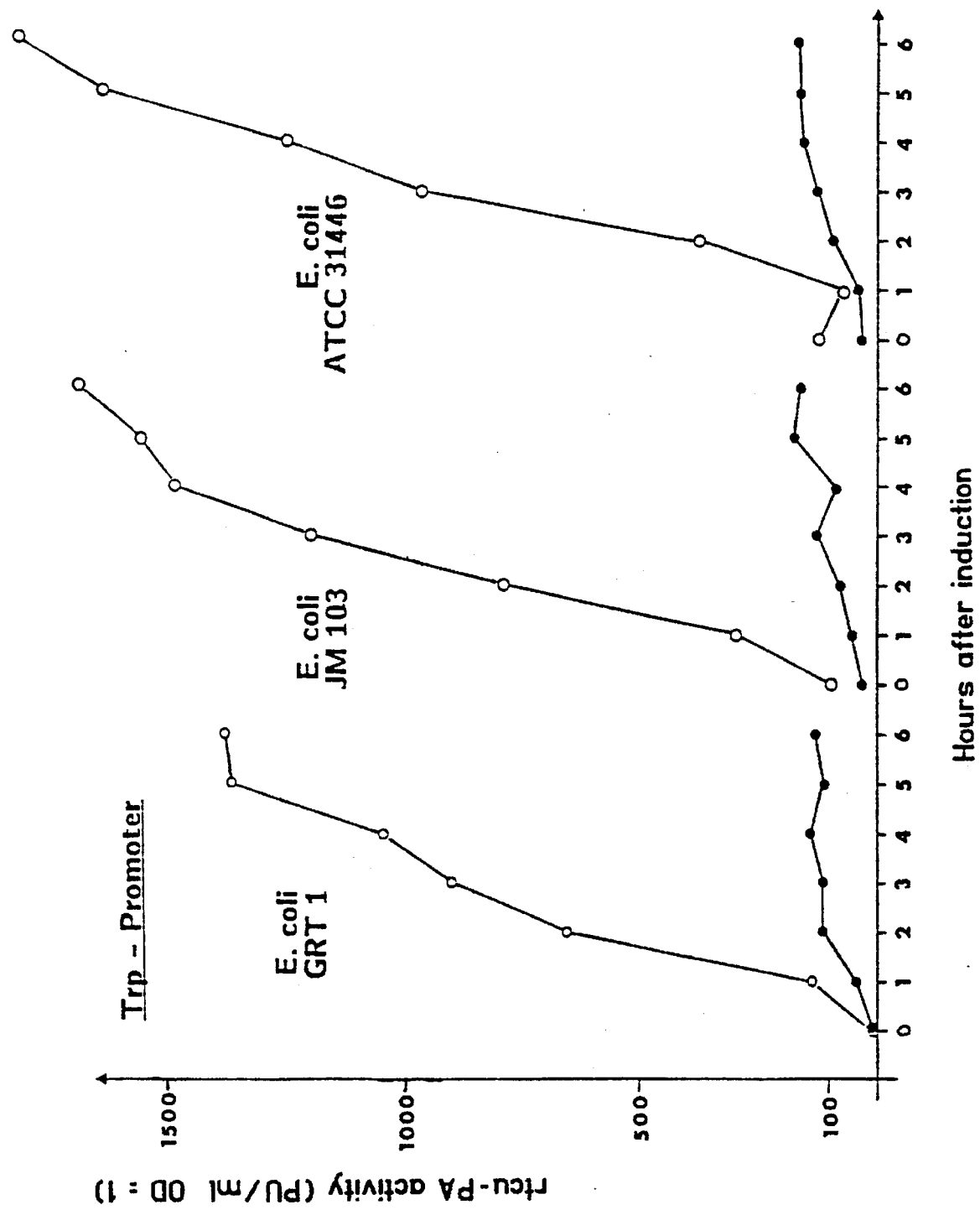
FIG. 10 illustrates expression of the intermediate protein of human recombinant scu-PA (determined as rtcu-PA activity after refolding of the intermediate protein and activation of the resulting recombinant scu-PA with plasmin) in different strains of *E. coli* transformed with the plasmid pBF 160 (o—o) or with the plasmid pUK 54 trp 207-1 (Holmes, W. E., Pennica, D., Blaber, M., Rey M. W., GUnzler, W. A., Steffens, G. J., Heynecker, H. L. *Biotechnol.* 3:923–929 (1985)) (●—●) under control by the trp-promotor and as function of time after induction with indoleacrylic acid. The rtcu-PA activities assayed with the substrate S2444 are given in Ploug units per ml of a culture medium having an optical density of 1 at 578 nm.
Figure 12:
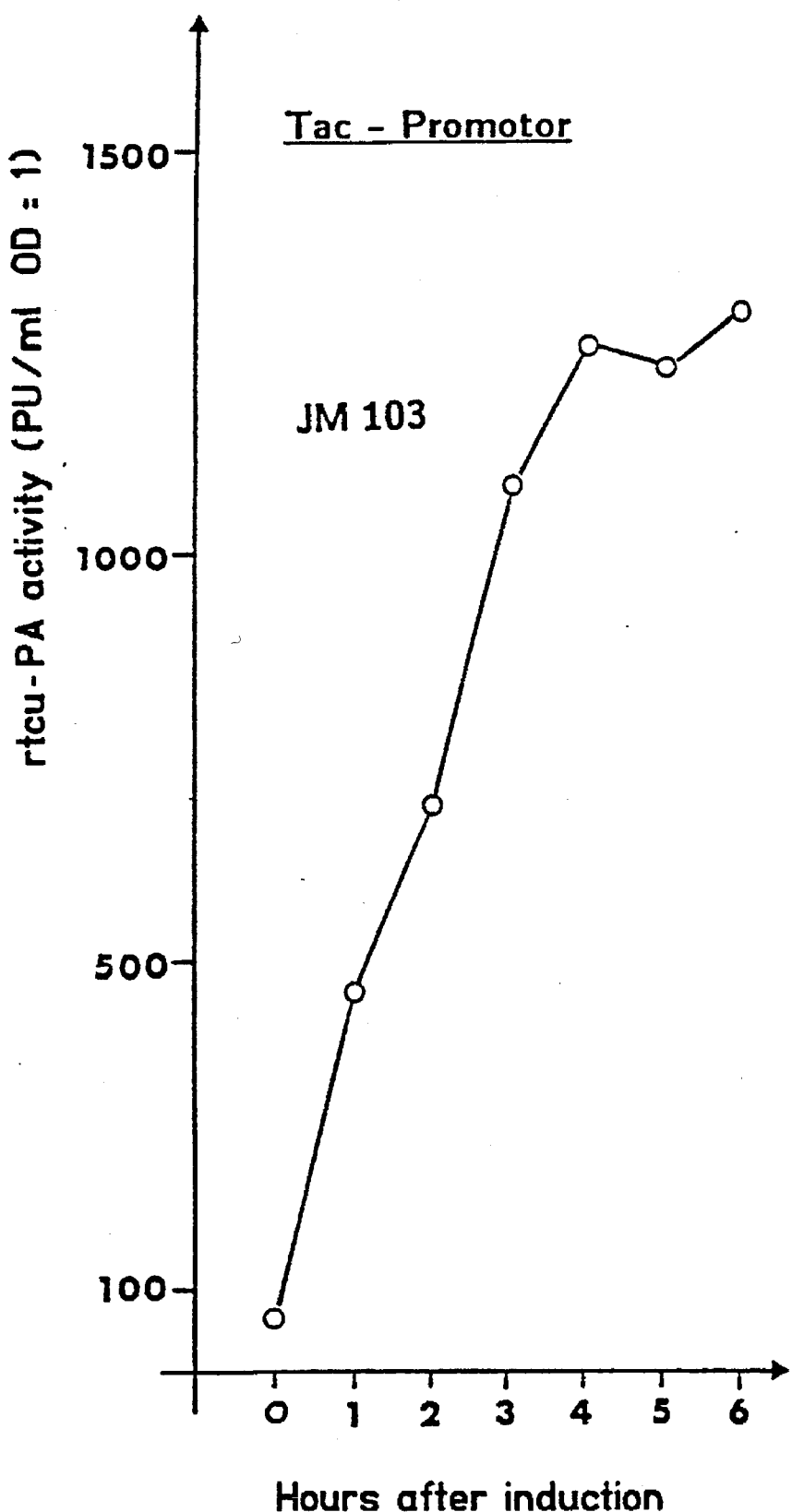
FIG. 12 shows expression rates of the intermediate protein of human recombinant scu-PA (determined as rtcu-PA activity after refolding and activation as explained above) in *E. coli* K12 JM103 transformed with the plasmid pBF 171, i.e. under control of the Tac-promotor. The induction was made at time zero by addition of IPTG. The rtcu-PA activities are given in Ploug units per ml of a culture medium having an optical density of 1.0 at 578 nm, assayed with the substrate S2444.
Figure 14:
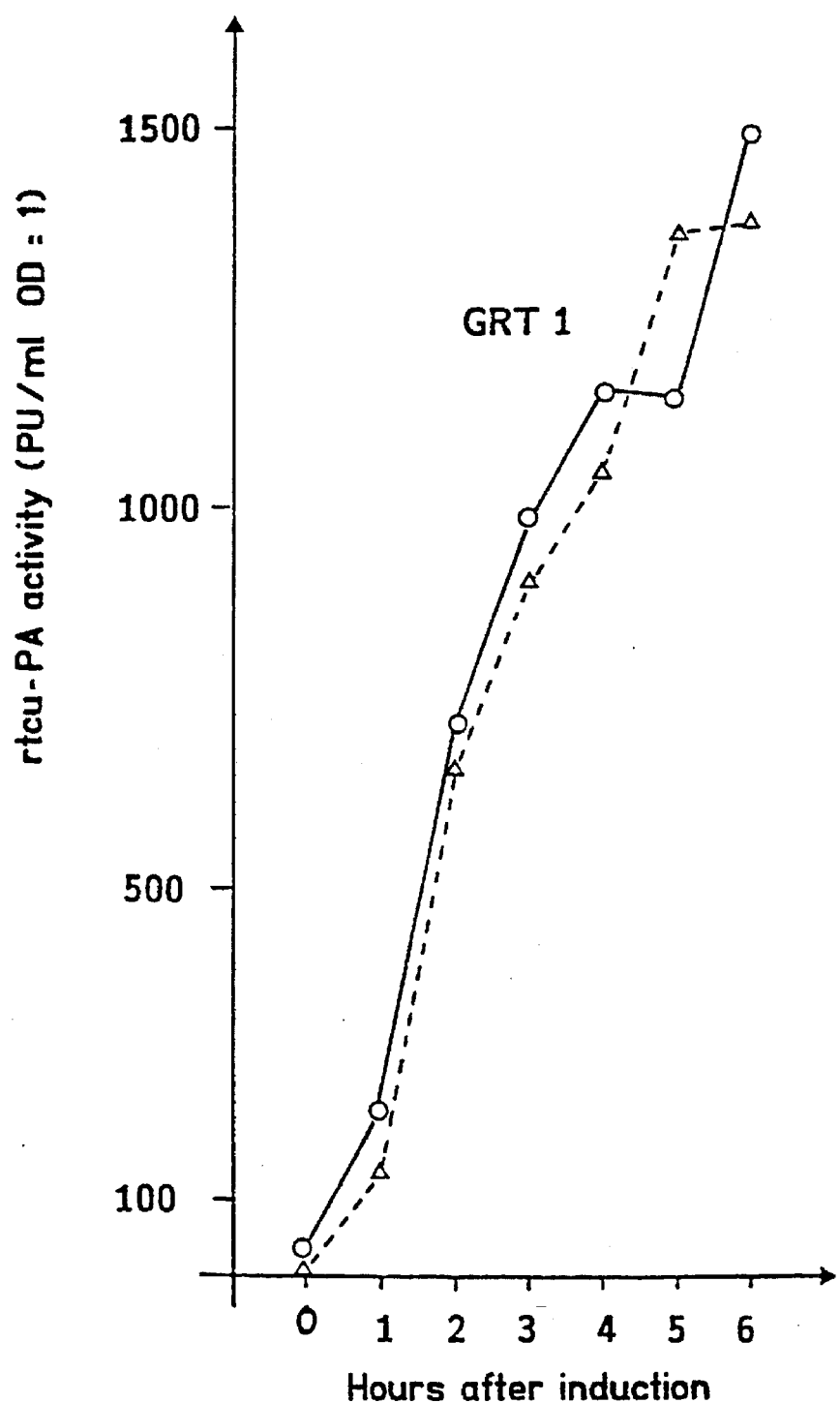
FIG. 14 depicts expression rates of the intermediate protein of human recombinant scu-PA in *E. coli* GRT-I transformed with the plasmid pBF 161 (o—o) or with the plasmid pBF 163 (Δ—Δ), i.e. in both cases under control of the Trp-promotor. Induction with indoleacrylic acid occurred at time zero. The rtcu-PA activities are given in Ploug units per ml of a culture medium having an optical density of 1.0 at 578 nm, assayed with the substrate S2444.

The yields of recombinant scu-PA obtained from intermediate protein prepared by using several different plasmids in different bacteria are shown in FIGS. 10, 12 and 14.

Figure 11A:
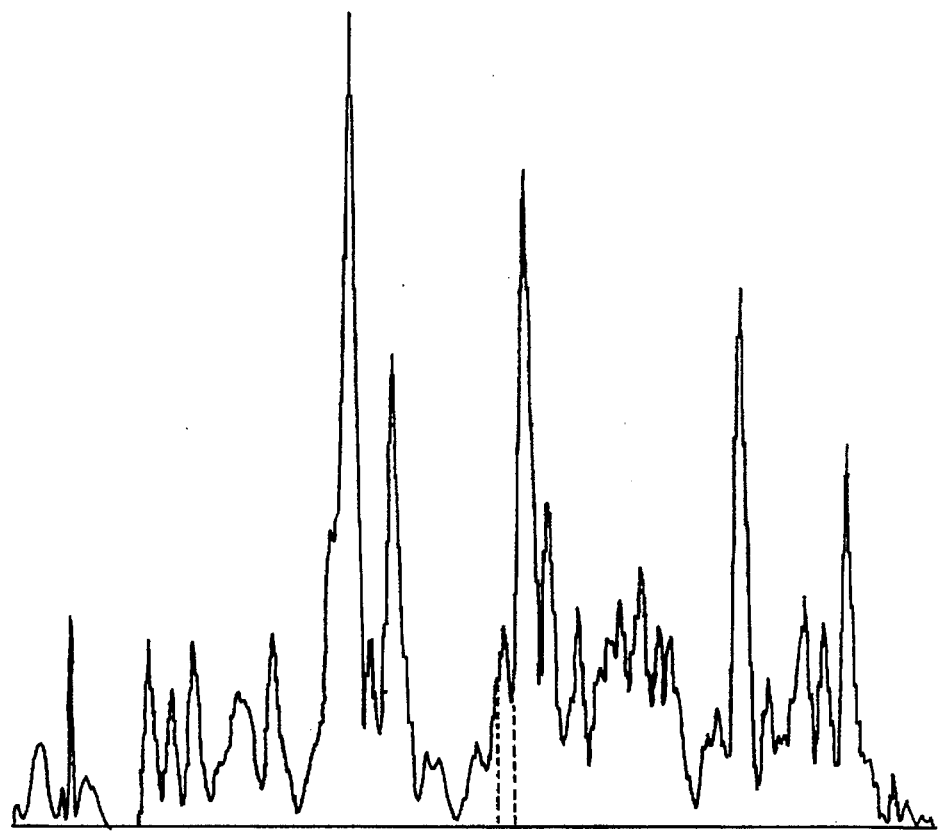
FIG. 11 is a densitogram of a SDS-PAGE of proteins from *E. coli* K12 JM103 cells transformed with pBF 161 obtained after cultivation (A) before, and (B) six hours after addition of indoleacrylic acid as inducer.
Figure 11B:
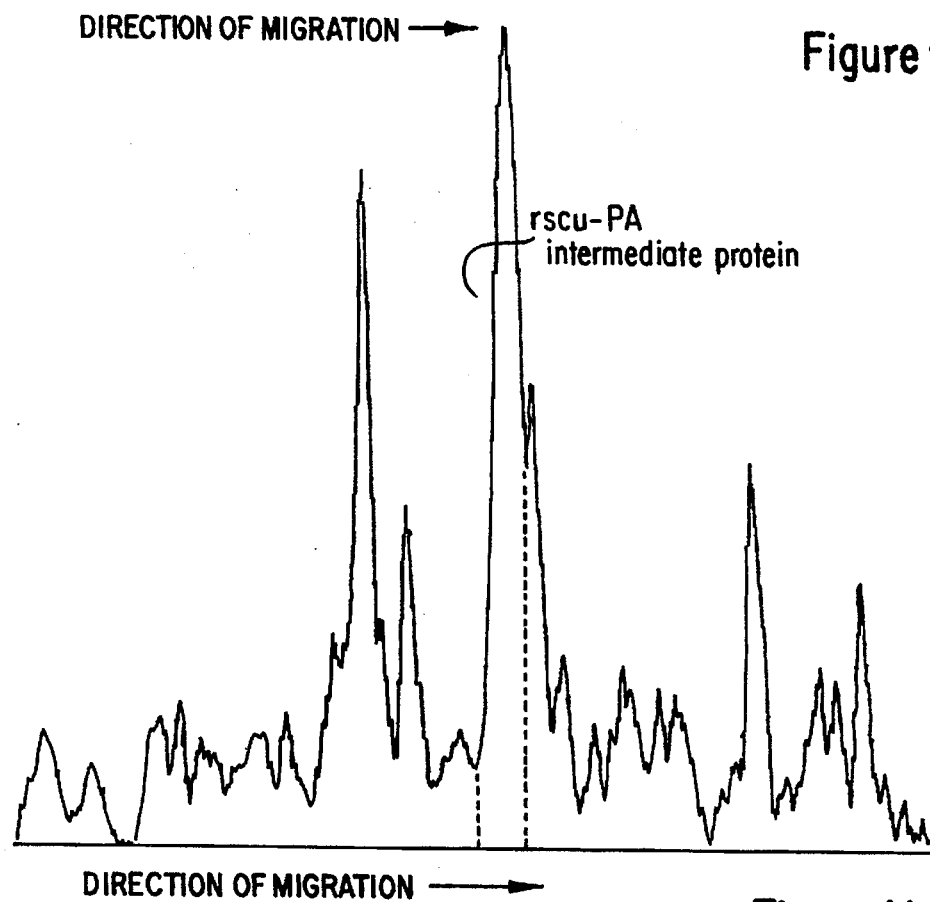

As can be seen from FIG. 11 as well as from the Examples given hereinafter—especially from Table 1 in Example 2—the plasmids according to the invention, preferably in strains of E. coli, cause production of the intermediate protein of recombinant scu-PA with an expression rate of 10 to 25 percent by weight, especially 14 to 20 percent by weight, of the total protein formed. Thus the expression rate when using the plasmids according to the invention is at least 10 to 15 times higher than that obtainable by using plasmids known in the art, such as pUK 54 trp 207-1.

The restriction enzymes used in the following Examples are commercially available (see, for instance, the survey given in *Nachr. Chem. Techn. Lab.* 35:939 (1987)).

The culture medium used in the Examples for the selection of clones contains per liter: 7.8 g of peptone from meat, 7.8 g of peptone from casein, 10 g of yeast extract, 5.6 g of sodium chloride and 10 g of glucose. This medium is mixed with 10 g/l of agar, heat-sterilized and poured into Petri dishes.

Unless otherwise specified, the term "ampicillin-containing medium" comprises the above culture medium to which 150 µg of ampicillin per ml were added.

EXAMPLE 1

Construction of the expression plasmid pBF 160 for the intermediate protein of recombinant scu-PA containing the synthetic scu-PA gene under control of the Trp-promotor.
a) Construction of the plasmid pBF 158 i) The nic/bom region, positioned between bases 2207 and 2263 (Winnacker, "Gene und Klone", VCH Verlagsgesellschaft, Weinheim, 1985, p. 298), is removed from the plasmid pBR 322 (Pharmacia, Nr. 27-4902, 4363 bp) as follows.

pBR 322 is cleaved with the restriction endonuclease Nde I and thus linearized. The sticky ends are filled in to give blunt ends (Maniatis, et al., "*Molecular Cloning*", *A Laboratory Manual*, Cold Spring Harbor Laboratory, 1982). Then the strand is cleaved at base 2068 with Pvu II, and the two blunt ends of the remaining part of pBF 322 are ligated by standard means using T4-ligase.

Thereafter, the ligation products are used for transforming competent *E. coli* K12 JM103 cells (ATCC 39403; Hanahan, "DNA cloning" Vol. 1, ed. , D. M. Glover, IRL Press, Oxford, 1985, pp. 109–135). The transformed cells are cultivated on ampicillin containing medium. From the obtained clones are selected those which contain the plasmid pBF 157. This plasmid pBF 157 differs from the starting plasmid in that the fragments Pst I×Bsp M II, Pst I×Bal I and Pst I×Ava I in pBF 157 each are shortened by 228 base pairs in comparison to those fragments contained in pBR 322. Further, pBF 157 no longer contains the singular restriction sites of pBR 322 for Pvu II and Nde I.

ii) By cleaving with Eco RV and Nru I, followed by ligation of the resulting blunt ends, a large part of the tetracycline resistance gene is deleted from pBF 157. *E. coli* K12 JM103 cells are transformed with the ligation products and cultivated on ampicillin containing medium. From the obtained clones are selected those containing the plasmid pBF 158 which is 787 nucleotides smaller than pBF 157 and differs from the latter by deletion of the Bam HI restriction site.

Transformation of bacterial strains with pBF 158 does not confer tetracycline resistance on the bacteria.

b) Construction of pBF 158-01: insertion of a synthetic multi-cloning site.

Figure 3:
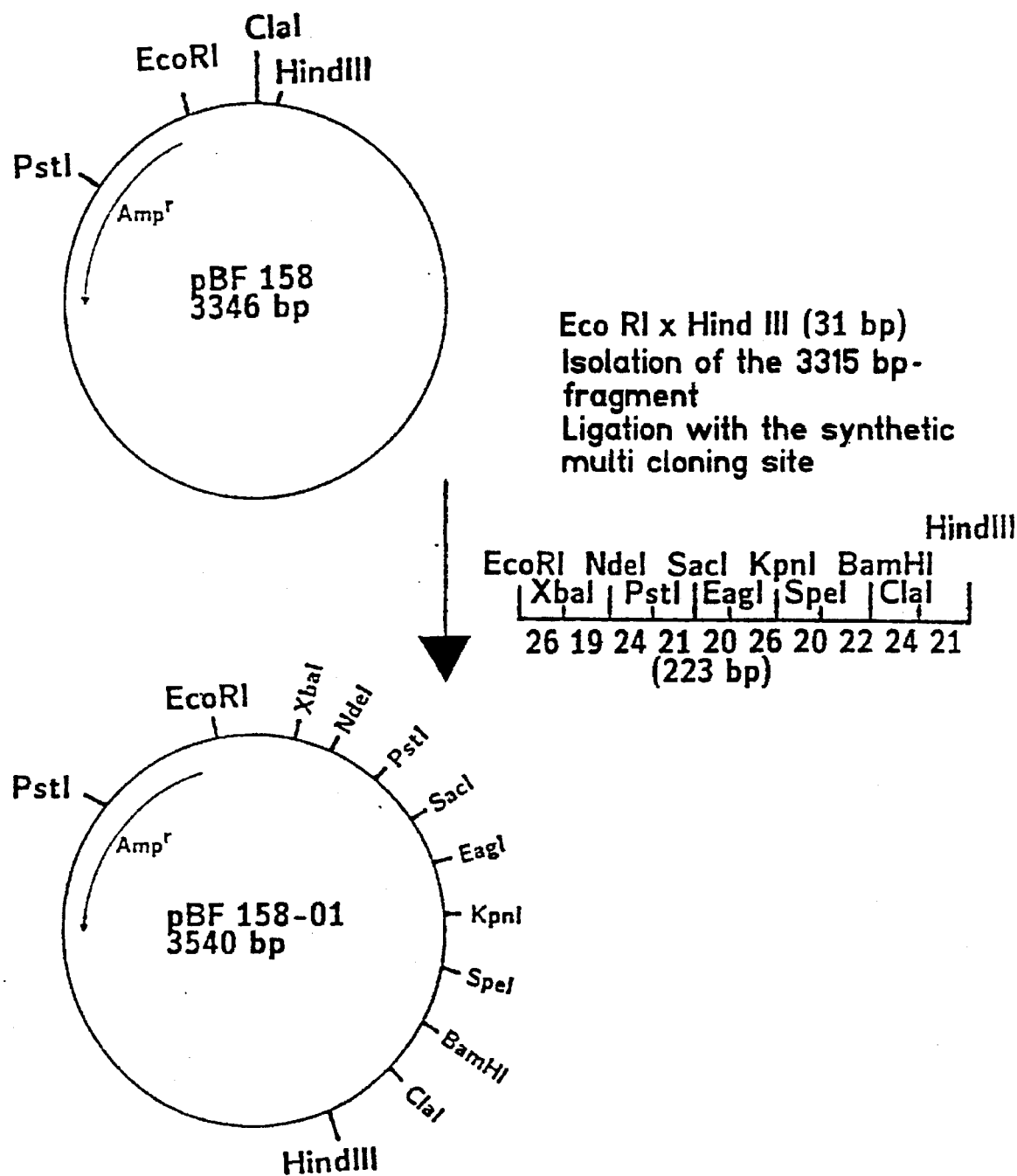
FIG. 3 outlines construction of the plasmid pBF 158-01, showing the insertion of the synthetic multi-cloning site into the plasmid pBF 158 between the restriction sites Eco RI and Hind III.

From pBF 158 a 31 bp fragment is deleted by cleavage with Eco RI and Hind III, and then the multi-cloning site, the sequence of which is shown in FIG. 2, is ligated between these restriction sites. *E. coli* K12 JM103 cells are transformed with the ligation products and then cultivated on ampicillin containing medium, whereupon clones containing the plasmid pBF 158-01 are selected. This plasmid differs from pBF 158 in that it additionally contains the singular restriction sites Xba I, Nde I, Sac I, Eag I, Kpn I and Spe I, and also a second Pst I restriction site (see, for example, FIG. 3).

c) Construction of pBF 158-01 T: insertion of a transcription terminator.

From pBF 158-01 the Cla I×Hind III fragment of the multi-cloning site was deleted by digestion with the respective restriction enzymes and replaced by the Cla I×Hind III fragment from pRT 61 (Jorgensen et al., *J. Bacteriol.*, 138:705–714 (1979)) which includes the tet A/orf L terminator from Tn 10 (Schollmeier et al., *Nuc. Acids Res.*, 13:4227–4237 (1985)).

Figure 4:
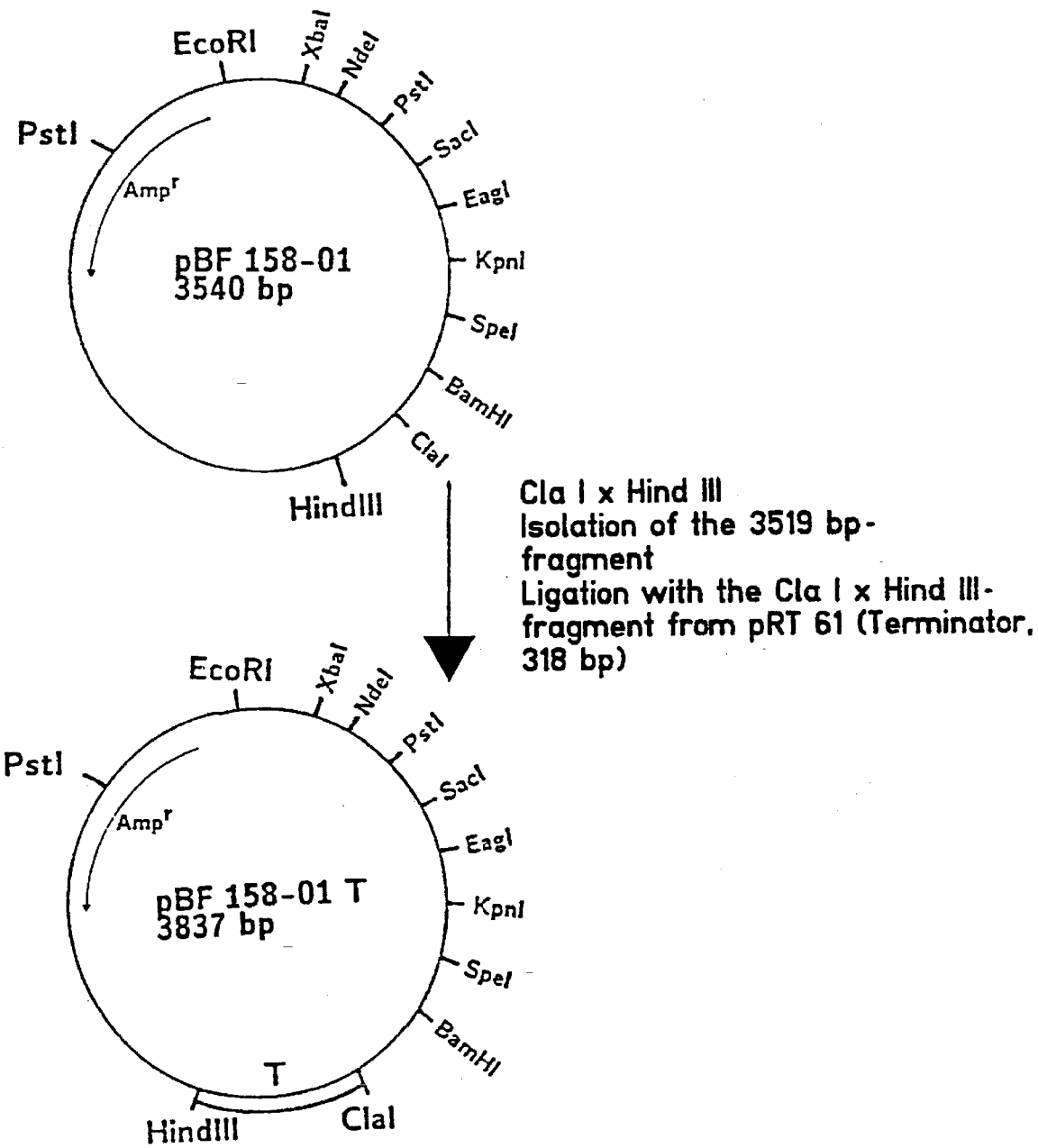
FIG. 4 shows the construction of the plasmid pBF 158-01 T in which the fragment Cla I×Hind III has been exchanged for the corresponding fragment "T" from the plasmid pRT 61 (Jorgensen, R. A. Reznikoff, W. S. *J. Bacteriol.* 138:705–714 (1979)) containing the tet A/orf L terminator from Tn 10 (Schollmeier, K., Gärtner, D., Hillen, W. *Nuc. Acids Res.* 13:4227–4237 (1985)).
Figure 6A:
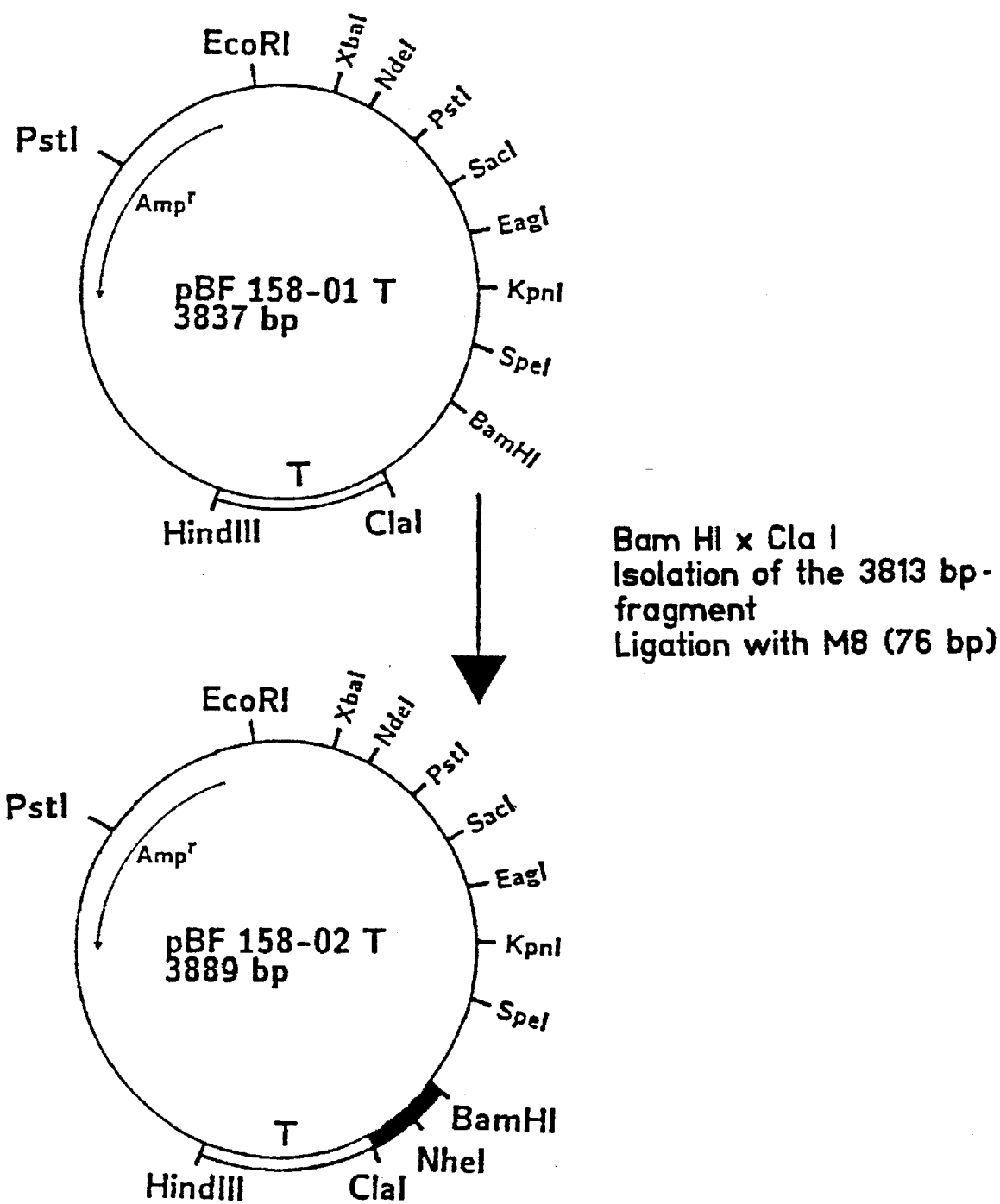
FIGS. 6a to 6c outline construction of the plasmids pBF 158-02 T to pBF 158-06 T by insertion of the oligonucleotide fragments M4 to M8 (starting at the C-terminus of the desired protein corresponding to the 3' terminus of the DNA strand) into the plasmid pBF 158-01-T.
Figure 6B:
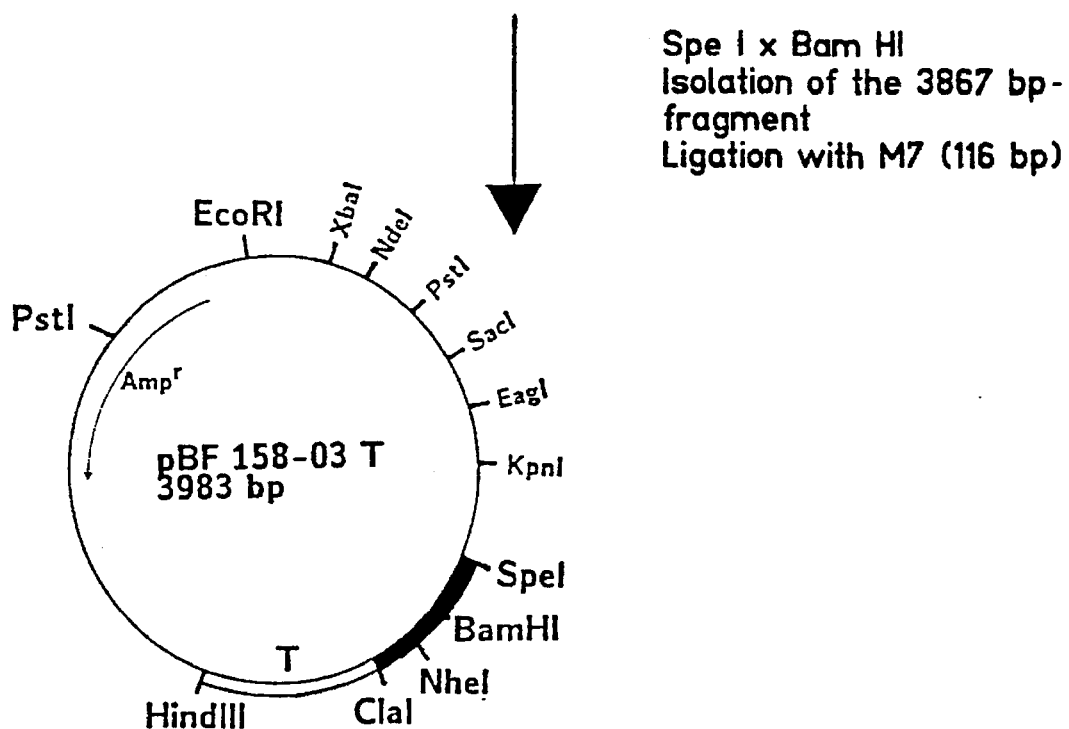
Figure 6C:
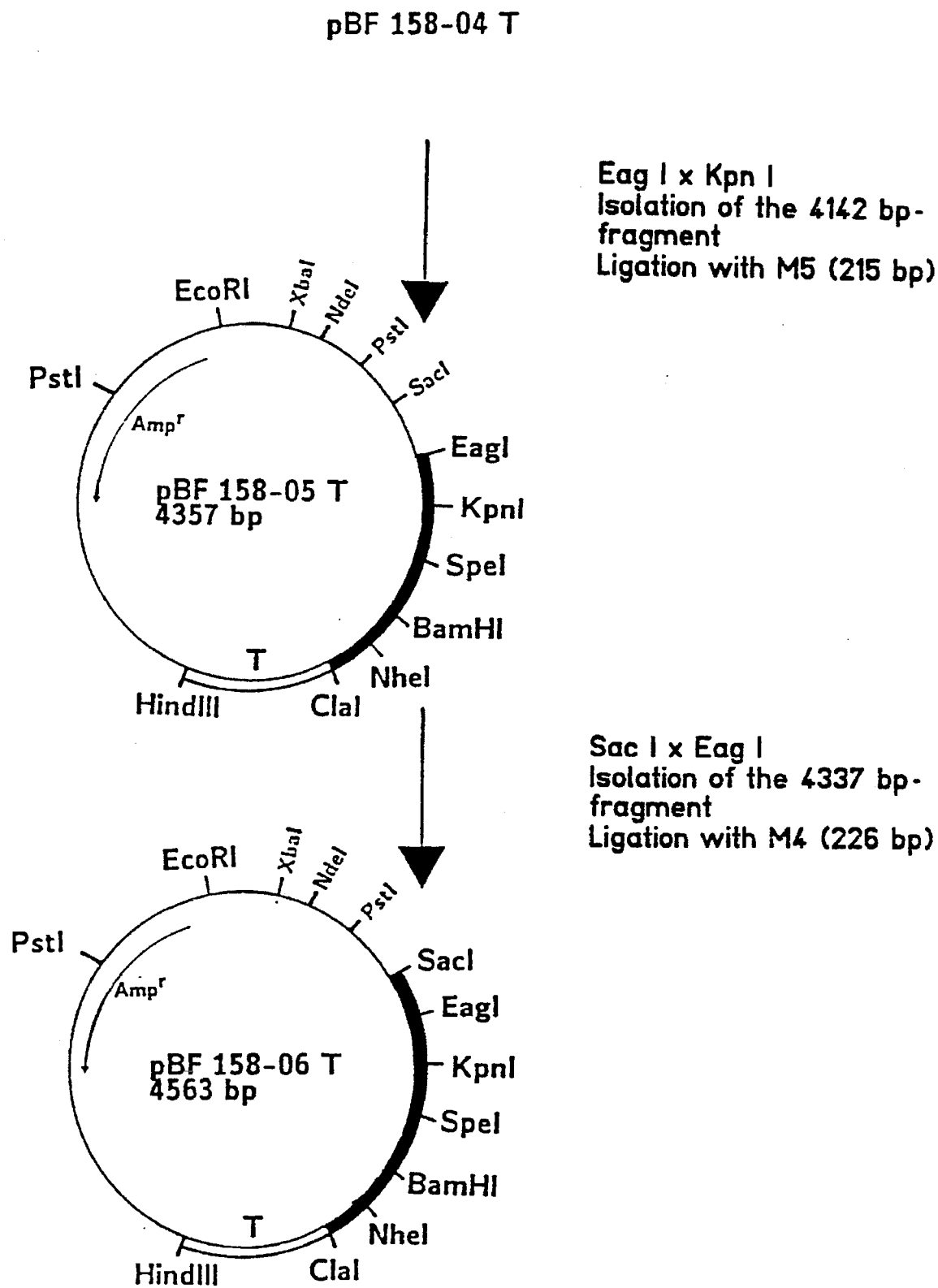

After transformation the strain *E. coli* K12 JM103 and cultivation on ampicillin-containing medium, such clones were selected which contain the plasmid pBF 158-01 T. This differs from pBF 158-01 in that its Cla I×Hind III fragment is enlarged by 297 nucleotides (see, for example, FIG. 4).

d) Construction of the plasmids pBF 158-02 T to pBF 158-06 T: insertion of the synthetic fragments M4 to M8 of the scu-PA gene.

The synthetic fragments are shown in FIGS. 5a to 5g. They were inserted into the respective vectors in the form of double-stranded fragments containing about 200 base pairs. To achieve this, the vectors were cleaved with the restriction enzymes corresponding to the restriction sites given hereinafter and then separated from the fragment to be deleted by agarose electrophoresis, electro-elution, and purification by chromatography on DE 52. Thereafter the obtained part of the vector was ligated with the respective double-stranded synthetic fragment by means of T4-ligase, and the ligation products were used for transformation of *E. coli* K12 JM103. Transformed strains were selected on ampicillin containing medium. The individual plasmids pBF 158-02 T to pBF 158-06 T were constructed as outlined below:

i) Ligation of the fragment M 8 between Bam H 1 and Cla I in the plasmid pBF 158-01 T forms plasmid PBF 158-02 T. The oligonucleotide 019 codes for the C-terminus of scu-PA. Downstream of the stop codon TAA follows a Nhe I restriction site followed by additional transcription termination sequences of the trp A terminator (Christie et al., *Proc. Natl. Acad. Sci. USA*, 78:4180–4184 (1981)) and the site for Cla I.

ii) Ligation of the fragment M 7 between Spe I and Bam HI in the plasmid pBF 158-02 T yields the plasmid pBF 158-03 T.

iii) Ligation of the fragment M 6 between Kpn I and Spe I in the plasmid pBF 158-03 T yields the plasmid pBF 158-04 T.

iv) Ligation of the fragment M 5 between Eag I and Kpn I in the plasmid pBF 158-04 T yields the plasmid pBF 158-05 T.

v) Ligation of the fragment M 4 between Sac I and Eag I in the plasmid pBF 158-05 T yields the plasmid pBF 158-06 T.

From the clones obtained according to steps (i) to (v) are selected those which differ from the respective preceding clone by the presence of the newly inserted fragment having the correct sequence as verified by DNA-sequencing.

e) Construction of the plasmid pBF 158-08 T: insertion of the synthetic fragments M2 and M3 of the scu-PA gene.

Figure 7C:
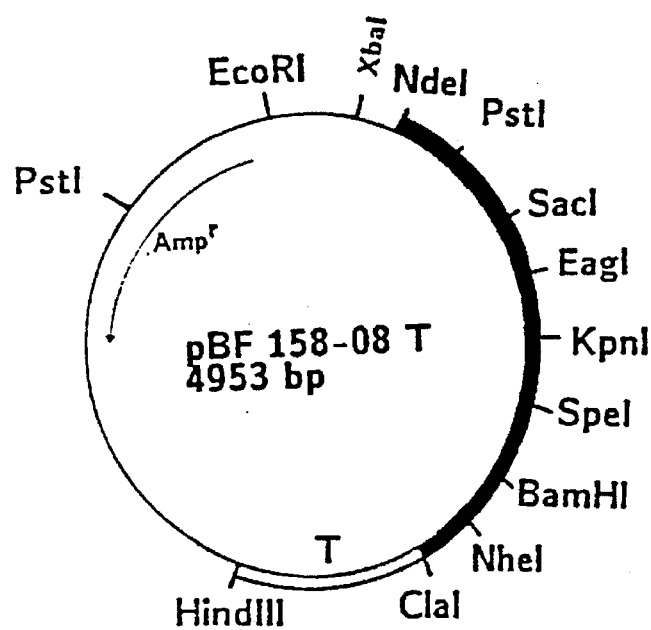
Figure 9:
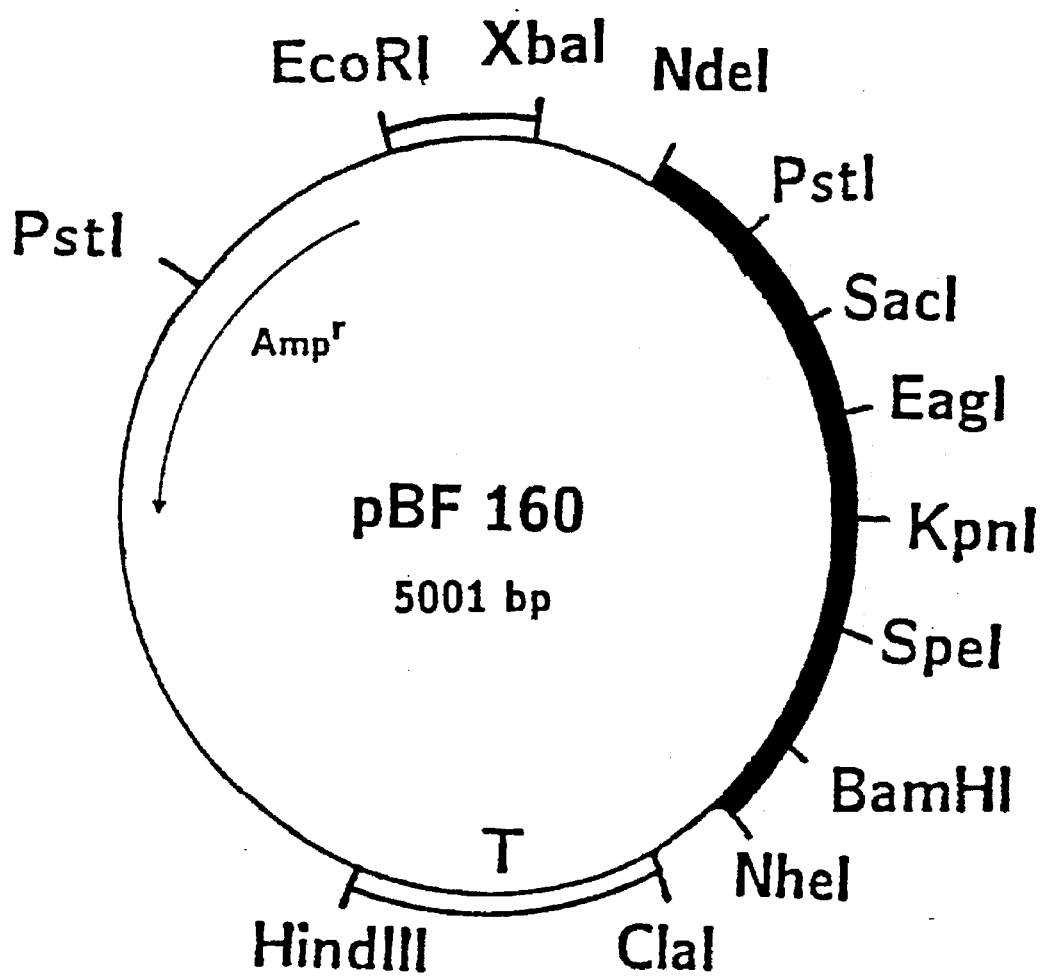
FIG. 9 outlines the construction of the expression plasmid pBF 160 suitable for expressing the intermediate protein of human recombinant scu-PA, in which the structural gene for scu-PA is shown by the black bar between the restriction sites Nde I and Cla I.

To insert the fragments M2 and M3, cleavage with Pst I is necessary. Therefore, an auxiliary construction in the plasmid pUC 19 has to be made since the plasmid pBF 158 (and its derivatives prepared in the foregoing Examples) contains a Pst I restriction site in the ampicillin resistance gene which would cause difficulties in the subsequent cloning steps (see, for example, FIGS. 7a to 7c).

i) From the commercially available plasmid pUC 19 the multi-cloning site and an additional 212 nucleotides upstream thereof were deleted as a Nde I×Hind III fragment. Into the plasmid pBF 158-02 T (see, for instance, Example 1(d)(i)) the oligonucleotide fragment M6 was inserted so that the plasmid pBF 158-04-3 T was obtained which corresponds to the plasmid pBF 158-04 T without the fragment M7. From the plasmid pBF 158-04-3 T the multi-cloning site was isolated as a Nde I×Hind III fragment which then was ligated with the fragment pUC 19/Nde I×Hind III. After transforming the ligation products in *E. coli* K12 JM103 cells and cultivating on ampicillin containing medium, those clones were selected which contained the plasmid pUC 19-04-3. This differs from pUC 19 by the presence of a Nde I×Hind III fragment of 712 bp.

ii) The Pst I×Sac I fragment was deleted from pUC 19-04-3, and the linearized vector was isolated and then ligated with the oligonucleotide fragment M3. *E. coli* K12 JM103 cells were transformed with the ligation products, followed by selection on ampicillin-containing medium. The selected clones contained the plasmid pUC-07 which differs from pUC 19-04-3 by a Pst I×Sac I fragment of 189 base pairs containing the fragment M3 with the correct sequence.

iii) From the plasmid pUC-07 obtained above the Nde I×Pst I fragment was deleted, and then the oligonucleotide fragment M2 was ligated between these restriction sites. *E. coli* K12 JM103 cells were transformed with the ligation products and cultivated on ampicillin-containing medium, after which those clones were selected which contained the plasmid pUC 19-08. This differs from the plasmid pUC 19-07 by the presence of the Nde I×Pst I fragment M2 (containing 246 bp) with the verified sequence.

iv) The fragments M2 and M3 were isolated from the plasmid pUC 19-08 as an Nde I×Sac I fragment and ligated into the larger part of pBF 158-06 T obtained from this plasmid by cleavage with Nde I and Sac I. *E. coli* K12 JM103 cells were transformed with the ligation products, followed by selection on ampicillin containing medium. Clones were selected which contain the plasmid pBF 158-08 T which differs from pBF 158-06 T by the presence of a Nde I×Sac I fragment of 435 bp.

f) Construction of the plasmid pBF 160: insertion of the synthetic Trp-promotor

The sequence of the Trp-promotor described by De Boer et al., *Proc. Natl. Acad. Sci. USA*, 80:21–25 (1983) was used up to the Xba I restriction site. Then the sequence 5'-AATTCTGAAT-3' was added to the 5'-terminus.

Thereby an Eco R I restriction site was constructed (see FIG. 8, fragment M1). The single strands 021 and 021 A were hybridized and then ligated into pBF 158-08 T digested with Eco R I×Xba I. *E. coli* K12 JM103 cells were transformed with the ligation products, cultivated on ampicillin-containing medium to select clones which contained pBF 160. This plasmid pBF 160 differs from all plasmids described above in Example 1 in that strains of *E. coli* transformed therewith produce the intermediate protein of recombinant scu-PA upon addition of indoleacrylic acid. Expression Test g) Fermentation Several strains of *E. coli* (for example, *E. coli* GRT-I, *E. coli* K12 JM103 and *E. coli* K12 ATCC 31446) transformed with the plasmid pBF 160 were cultivated under identical conditions in a medium containing 38 mM ammonium sulfate, 56 mM phosphate buffer having a pH of 7.0, 1 mM magnesium sulfate, 10 g of yeast extract/l, 10 g/l of glucose and 150 mg/l of ampicillin, and then the expression of the intermediate protein of recombinant scu-PA was induced by adding 62 mg/l of indoleacrylic acid.

For comparison purposes the same *E. coli* strains were transformed with a plasmid known in the art and containing the gene coding for human prourokinase from a CDNA bank, which was obtained by using Detroit 562 cell mRNA (Holmes et al., *Biotechnol.*, 3:923–929 (1985)) and which is known under the designation pUK 54 trp 207-1. These transformed strains then were cultivated and subjected to induction under the same conditions as described above for the strains transformed with plasmids according to the invention.

Prior to the induction and for 6 hours every hour after induction, samples of cells corresponding to 1 ml of a cell suspension having an optical density (OD) of 1 at 578 nm were separated and used for the determination of the expression rate.

ii) Refolding of the intermediate protein of recombinant scu-PA, the cleavage thereof to form rtcu-PA and assay of activity.

The cells isolated by centrifugation were lysed as described above by treatment with lysozyme, and then the homogenate of the lysed cells were used for the assay as described.

The expression rates determined by assay of the activity of the rtcu-PA obtained from the recombinant scu-PA (prepared by refolding of the intermediate protein) are shown in FIG. 10. As can be seen, the strains transformed with the plasmid pBF 160 produced an expression yield 10 to 15 times higher than that obtained with the same strains of *E. coli* which were transformed with the plasmid pUK 54 trp 207-1 known from the literature (Holmes et al., Supra). Moreover it is evident from these experiments that the expression yields in different strains, transformed with the same plasmid reach about the same values, i.e., that especially the *E. coli* strains transformed with the plasmid pBF 160 (regardless of the specific *E. coli* strain) in each case produced expression rates several times higher than those obtained from strains transformed with the known plasmid pUK 54 trp 207-1.

EXAMPLE 2

Construction of the expression plasmid pBF 161 for the intermediate protein of recombinant scu-PA containing the synthetic scu-PA gene under control of the Trp-promotor.

a) Plasmid construction.

The plasmid pBF 322 was cleaved with the restriction enzymes Eco RI and Hind III. The resulting 31 bp fragment was removed by agarose gel electrophoresis. The remaining part of pBF 322 was eluted from the gel by electroelution and then purified by chromatography over DE-52.

The plasmid pBF 160 (Example If) also was cleaved by Eco RI and Hind III. The Eco RI×Hind III fragment consisting of 1684 bp and containing the synthetic scu-PA gene with all regulatory units (Trp-promotor) was separated by agarose gel-electrophoresis, eluted from the gel by electroelution and purified using DE-52.

The two purified fragments thus obtained were ligated in the usual manner by means of T4-ligase, and then *E. coli* K12 JM103 was transformed with the ligation products. After cultivation on ampicillin containing medium, clones were selected which contained a 1684 bp Eco RI×Hind III fragment and which upon addition of indoleacrylic acid produce the intermediate protein of recombinant scu-PA. These clones contain the plasmid pBF 161.

b) Expression Test.

The strains *E. coli* GRT-I, *E. coli* K12 JM103 and *E. coli* K12 ATCC 31446 were transformed with the plasmid pBF 161, and then the fermentation and the assays for expression were carried out as described in Example 1(g). The yields of intermediate protein of recombinant scu-PA determined as rtcu-PA activity one to six hours after induction were comparable to those obtained with the same strains transformed with the plasmid pBF 160 shown in FIG. 10.

The cell mass obtained by centrifugation (i.e., in the same manner as described in Example 1(g)) may also be lysed by boiling in 0.25M Tris HCl buffer having a pH of 8.0 in the presence of 4% SDS, 1% mercaptoethanol and 20% glycerol. The resulting proteins in dissolved form were separated by SDS-PAGE and visualized in the gel by Coomassie blue staining. The stained gels were evaluated densitometrically, and the areas under the peaks were integrated. The amount of the intermediate protein of recombinant scu-PA formed was determined by integrating the band appearing after induction with indoleacrylic acid corrected for the protein detected in the very same area prior to induction. FIG. 11 shows a densitogram of the proteins obtained from E. coli K12 JM103 cells transformed with pBF 161. In the Example shown, the yield of the intermediate protein of recombinant scu-PA after induction amounts to 17.9 percent by weight of the total bacterial protein. Additional Examples are given in the following Table 1:

TABLE 1

Expression level of intermediate protein of recombinant scu-PA expressed as percent of total bacterial protein

| Strain of E. coli | Plasmid | |
|---|---|---|
| | pBF 161 | pUK 54 trp 207-1 |
| K12 ATCC 31446 | 14 | 1.5 |
| K12 JM103 | 17.9 | 1.9 |
| GRT-I | 17.8 | 1.7 |

EXAMPLE 3

Construction of an expression plasmid for intermediate protein of recombinant scu-PA containing the synthetic scu-PA gene under control of the Trp promotor in pBF 322 with a deletion in the tetracycline resistance gene.

a) Construction of the plasmid pBR322 del.

The plasmid pBR 322 was cleaved with the restriction endonucleases Eco RV and Nru I. The resulting 787 bp fragment was removed by agarose gel electrophoresis. The remaining portion of pBF 322 was eluted from the gel by electroelution and then purified by chromatography over DE 52. The blunt ends of this remaining part pBR 322/Eco RV×Nru I were ligated by means of T4-ligase in the usual manner. After transformation of E. coli K12 JM103 by the ligation products and cultivation on ampicillin-containing medium, clones were selected which did not grow when transferred to a medium containing 25 µg of tetracycline per ml, i.e., they did not exhibit tetracycline resistance. These clones contained the plasmid pBF 322 del which differs from pBF 322 in that it is smaller by 787 bp and in that it is not clearable by Eco RV and Nru I.

b) Construction of the plasmid pBF 162.

The plasmid pBF 322 del was cleaved with Eco RI and Hind III. The resulting 31 bp fragment was removed by preparative agarose gel electrophoresis and the remaining part of pBF 322 del was eluted from the gel by electroelution and then purified by chromatography over DE 52.

Proceeding as above but starting from pBF 160, the Eco RI×Hind III fragment consisting of 1684 bp and containing the synthetic scu-PA gene with all regulatory units (Trp-promotor) was obtained.

Both fragments prepared in this Example 3(b) were ligated in the usual manner by means of T4-ligase, and then the ligation products were used for the transformation of E. coli K12 JM103 cells, followed by cultivation on ampicillin-containing medium. Thereafter, clones were selected which contained a 1684 bp Eco RI×Hind III fragment and which, after adding 62 µg of indoleacrylic acid per ml, produced the intermediate protein of recombinant scu-PA. These clones harbor the plasmid pBF 162.

c) Expression test.

E. coli GRT-I was transformed with pBF 162, and then the fermentation and the expression assay were carried out as described in Example 1(g). The yield of intermediate protein of recombinant scu-PA six hours after induction (determined as rtcu-PA activity) was 1,300 PU/ml of a cell suspension having an optical density of 1 and was comparable to the yield obtained by expression after transformation of E. coli GRT-I with the plasmid pBF 160 shown in FIG. 10.

EXAMPLE 4

Construction of the expression plasmid pBF 171 for the intermediate protein of recombinant scu-PA containing the synthetic scu-PA gene under control of the Tac-promotor.

a) Plasmid construction.

The plasmid pBF 161 was cleaved with Eco RI and Xba I. The resulting 74 bp fragment was removed by preparative agarose gel electrophoresis, and the remaining part of the plasmid was eluted by electrophoresis from the gel and then purified by chromatography over DE 52.

From the plasmid ptac SDT (DSM 5018) the Eco RI×Xba I fragment which contains the Tac-promotor was isolated by cleaving ptac SDT with Eco RI×Xba I and isolating the desired fragment by preparative PAGE.

The fragment was eluted from the mechanically disintegrated polyacrylamide by heating to 65° C. in ammonium acetate/SDS buffer having a pH of 8.0 and purified by repeated extraction with phenol, saturated with 1M Tris-buffer having a pH of 8.

Both fragments thus obtained in this Example 4(a) were ligated in the usual manner by means of T4-ligase, and then the ligation products were used for the transformation of E. coli K12 JM103. After cultivation on ampicillin containing medium, those clones were selected which after addition of IPTG produced the intermediate protein of recombinant scu-PA. These clones contained the plasmid pBF 171.

b) Expression test.

E. coli K12 JM103 was transformed with pBF 171 and then the fermentation and the assays of the expression were carried out as described in Example 1(g) whereby, however, IPTG (final concentration 0.5 mM) was used for the induction.

The yields of intermediate protein of recombinant scu-PA determined as rtcu-PA activity 1 to 6 hours after induction are shown in FIG. 12. They are comparable to those obtained by using the plasmid pBF 160 in the same strain of E. coli which are shown in FIG. 10.

EXAMPLE 5

Construction of the expression plasmid pBF 172 for the intermediate protein of recombinant scu-PA in which the synthetic scu-PA gene is under control of the Tac-promotor in pBF 322 with a deletion in the tetracycline resistance gene.

a) Plasmid Construction.

The plasmid pBR 322 del (described in Example 3(a)) was cleaved with Eco RI×Hind III. The resulting 31 bp fragment was removed by preparative agarose gel-electrophoresis, and the remaining part of pBF 322 was eluted from the gel by electroelution and then purified by chromatography over DE 52.

Proceeding in the same manner but using the plasmid pBF 171 (obtained in Example 4(a)) the Eco RI×Hind III fragment therefrom was obtained containing the synthetic scu-PA gene with all regulatory units (Tac-promotor).

Both fragments obtained in this manner were ligated in the usual manner by means of T4-ligase and then the ligation products were used for the transformation of *E. coli* K12 JM103 cells. After cultivation on ampicillin containing medium, clones were selected which, in the presence of 0.5 mM IPTG, produced the intermediate protein of recombinant scuPA.

These clones harbor the plasmid pBF 172.

b) Expression test.

*E. coli* K12 JM103 was transformed with pBF 172, and then the fermentation and the expression assays were carried out as described in Example 1(g) except that IPTG (final concentration 0.5 mM) was used for the induction. The yields of intermediate protein of recombinant scu-PA determined as rtcu-PA activity one to six hours after induction were about 1,100 PU/ml of a cell suspension having an optical density of 1 and were comparable to those obtained by use of the plasmid pBF 160 in the same strain of *E. coli* which are shown in FIG. 10.

EXAMPLE 6

Modification of the distance between the Shine-Dalgarno sequence and the start codon in an expression plasmid for the intermediate protein of recombinant scu-PA.

In all constructions described in Examples 1 through 5, the start codon ATG forms a part of a Nde I restriction site-CATATG-. Nde I cleaves this hexanucleotide sequence after the first A, whereby 5'-protruding termini are formed. By filling in the 3'-end, i.e., constructing blunt ends, and religating, the sequence in question becomes enlarged by two base pairs. By proceeding in this manner, the Nde I restriction site is also eliminated. As can be seen from FIG. 13 in the Example shown, the distance from the S.D. sequence to the start codon is enlarged from 8 to 10 base pairs. The experimental procedure for accomplishing this is illustrated by the following Example.

a) Construction of the plasmid pBF 163.

The plasmid pBF 161 was cleaved with Nde I, and then the sticky ends were filled in with the Klenow fragment of DNA-polymerase I (Maniatis et al., supra). Thereafter the DNA was ligated in the usual manner by means of T4-ligase, and then the ligation products were used for the transformation of *E. coli* K12 JM103, followed by selection on ampicillin-containing medium. Clones harboring the plasmid pBF 163 were selected. This plasmid differs from pBF 161 by the absence of a Nde 1 restriction site and by the additional bases—TA—in the region of the former Nde I restriction site (see, for example, FIG. 13).

b) Expression test.

*E. coli* GRT-I was transformed with the plasmid pBF 163, and then the fermentation and the assays of the expression were carried out as described in Example 1(g). The yields of intermediate protein of recombinant scuPA (determined after refolding and activation as rtcu-PA activity per ml of a cell suspension having an optical density of 1.0) one to six hours after induction with 62 mg of indoleacrylic acid per liter are shown in FIG. 14.

They are comparable to those obtained by use of the plasmid pBF 160 in the same strain of *E. coli* which are shown in FIG. 10.

The foregoing description and examples have been set forth merely to illustrate the invention and are not intended to be limiting. Since modifications of the described embodiments incorporating the spirit and substance of the invention may occur to persons skilled in the art, the scope of the invention should be construed to include all modifications falling within the ambit of the appended claims and equivalents thereof.

What is claimed is:

1. An operon for use in the manufacture of the human single chain urinary plasminogen activator (recombinant scu-PA) in a strain of *Escherichia coli*, comprising in 5' to 3' order the following operatively linked elements: a regulatable promotor selected from the group consisting of a Trp promotor and a Tac promotor; a Shine-Dalgarno sequence effective as a ribosomal binding site, a translational start codon, a structural gene for single chain urinary plasminogen activator having the nucleotide sequence of FIG. 15 and downstream of said structural gene at least one transcription terminator, wherein said Shine-Dalgarno sequence is separated from said start codon by from 6 to 12 nucleotides, and wherein further, said operon effects the synthesis in inclusion bodies of an inactive form of said single chain urinary plasminogen activator in a strain of *Escherichia coli* with an expression rate of from about 10 to about 25 percent by weight of the total protein produced.

2. The operon of claim 1, comprising two transcription terminators downstream of said structural gene.

3. A plasmid comprising the operon of claim 1, wherein said plasmid is suitable for expression of said operon in a strain of *Escherichia coli*.

4. The operon according to claim 1, wherein said Shine-Dalgarno sequence is separated from said start codon by from 8 to 10 nucleotides.

5. The operon of claim 1, wherein said regulatable promotor is a Trp promotor having the nucleotide sequence of FIG. 8.

6. The operon of claim 1, wherein said regulatable promotor is the Tac promotor from the plasmid ptac SDT (DSM 5018).

7. The operon of claim 2, wherein one of said terminators is a trp A terminator or a tet A/orf L terminator from transposon Tn 10.

8. The plasmid of claim 3, wherein said plasmid comprises the plasmid pBR 322 from which the nic/bom region has been removed.

9. The plasmid of claim 3, wherein said plasmid is the plasmid pBR 322 in which the tetracycline resistance gene has been mutated such that said plasmid does not express tetracycline resistance.

10. The plasmid according to claim 3 wherein said plasmid is the plasmid pBR 322 from which the nic/bom region has been removed and in which the tetracycline resistance gene has been mutated such that said plasmid does not express tetracycline resistance.

11. The plasmid according to claim 10, selected from the group consisting of the plasmids pBF 160, pBF 161, pBF 162 and pBF 163.

12. The plasmid of claim 11, that is designated pBF 160.

13. A plasmid according to claim 10, selected from the group consisting of the plasmids pBF 171 and pBF 172.

14. The operon of claim 1, wherein said strain of *Escherichia coli* is of the subgroup *Escherichia coli* K12.

15. An operon according to claim 1, which effects the synthesis in inclusion bodies of an inactive form of said single chain urinary plasminogen activator with an expression rate of from about 14 to about 20 percent by weight of the total protein produced.

16. A process for producing a plasmid according to claim 3 comprising the steps of:

(i) removing the nic/bom-region and mutationally inactivating the tetracycline resistance gene of pBR 322;

(ii) inserting a multi-cloning site having the nucleotide sequence of FIG. 2 between the pBR 322 restriction sites Eco RI and Hind III; and (iii) inserting by means of said multi-cloning site a transcription terminator, a synthetic gene encoding scu-PA, and a Trp-promotor such that said gene is operatively linked to said promoter and to said terminator.

17. The process according to claim 16 further comprising inserting an Eco RI×Hind III fragment comprising the multi-cloning site and said promoter and said terminator into another plasmid which can replicate in a strain of *Escherichia coli*.

18. A process for producing a plasmid according to claim 16 or claim 17 wherein the spacing between the Shine-Dalgarno sequence and the start codon is enlarged, comprising the additional steps of cleaving plasmid with the restriction enzyme Nde I to form sticky ends, filling in the resulting sticky ends to form blunt ends, and ligating the resulting blunt ends.

19. A host cell transformed by a plasmid according to claim 3 wherein said host cell is a strain of *Escherichia coli*.

20. A process for producing human single chain urinary plasminogen activator (recombinant scu-PA) comprising the steps of: transforming cells of a strain of *Escherichia coli* with a plasmid according to claim 3, inducing expression of said scu-PA structural gene in said cells or their progeny, separating the resulting inactive form of recombinant scu-PA from said cells, solubilizing said inactive form of recombinant scu-PA, and refolding said inactive form of recombinant scu-PA by the action of a redox system to form active recombinant scu-PA.

* * * * *